(12) United States Patent
Biggadike et al.

(10) Patent No.: US 7,402,598 B2
(45) Date of Patent: Jul. 22, 2008

(54) ARYLETHANOLAMINE $\beta_2$-ADRENORECEPTOR AGONIST COMPOUNDS

(75) Inventors: Keith Biggadike, Stevenage (GB); Diane Mary Coe, Stevenage (GB); Duncan Stuart Holmes, Stevenage (GB); Brian Edgar Looker, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 190 days.

(21) Appl. No.: 10/522,321

(22) PCT Filed: Jul. 24, 2003

(86) PCT No.: PCT/EP03/08264

§ 371 (c)(1),
(2), (4) Date: Jul. 6, 2005

(87) PCT Pub. No.: WO2004/016578

PCT Pub. Date: Feb. 26, 2004

(65) Prior Publication Data

US 2006/0111344 A1 May 25, 2006

(30) Foreign Application Priority Data

Jul. 25, 2002 (GB) .................... 0217225.2

(51) Int. Cl.
*A61K 31/47* (2006.01)
*C07D 215/22* (2006.01)

(52) U.S. Cl. .................. 514/312; 546/157; 546/158; 546/290; 544/105; 548/165; 564/90; 514/230.5; 514/345; 514/367; 514/604

(58) Field of Classification Search .......... 514/312, 514/230.5, 345, 367, 604; 546/157, 158, 546/290; 544/105; 548/165; 564/90
See application file for complete search history.

(56) References Cited

U.S. PATENT DOCUMENTS

| 3,994,974 | A | 11/1976 | Murakami et al. |
| 4,730,008 | A | 3/1988 | Skidmore et al. |
| 4,853,381 | A | 8/1989 | Finch et al. |
| 4,853,382 | A | 8/1989 | Skidmore et al. |
| 4,908,386 | A | 3/1990 | Finch et al. |
| 4,937,268 | A | 6/1990 | Skidmore et al. |
| 4,963,564 | A | 10/1990 | Skidmore et al. |
| 4,990,505 | A | 2/1991 | Skidmore et al. |
| 4,992,474 | A | 2/1991 | Skidmore et al. |
| 4,997,986 | A | 3/1991 | Mitchell et al. |
| 5,066,678 | A | 11/1991 | Finch et al. |
| 5,099,068 | A | 3/1992 | Mitchell et al. |
| 5,109,023 | A | 4/1992 | Mitchell et al. |
| 5,283,262 | A | 2/1994 | Mitchell et al. |
| 5,552,438 | A | 9/1996 | Christensen, IV |
| 6,395,738 | B1 | 5/2002 | Ohshima et al. |
| 6,514,996 | B2 | 2/2003 | Ohshima et al. |
| 6,716,987 | B1 | 4/2004 | Ohshima et al. |
| 2002/0012829 | A1 | 1/2002 | Yamahira et al. |

FOREIGN PATENT DOCUMENTS

| DE | 3524990 | 1/1986 |
| DE | 4028398 | 3/1992 |
| EP | 69715 | 1/1983 |
| EP | 0162576 | 11/1985 |
| EP | 0220054 | 4/1987 |
| EP | 220878 | 5/1987 |
| EP | 223410 | 5/1987 |
| EP | 286242 | 10/1988 |
| EP | 303465 | 2/1989 |
| EP | 317206 | 5/1989 |
| EP | 416951 | 3/1991 |
| GB | 2064336 | 6/1981 |
| GB | 2129691 | 5/1984 |
| GB | 2140800 | 12/1984 |
| GB | 2159151 | 11/1985 |
| GB | 2162842 | 2/1986 |
| GB | 2169265 | 7/1986 |
| GB | 2178965 | 2/1987 |
| GB | 2230523 | 10/1990 |
| GB | 416951 | 9/1991 |
| GB | 2242134 | 9/1991 |
| WO | 95/01170 | 1/1995 |
| WO | WO 95/19336 | 7/1995 |
| WO | 99/16766 | 4/1999 |
| WO | 99/47505 | 9/1999 |
| WO | 01/13953 | 3/2001 |

OTHER PUBLICATIONS

Thornber, C.W.; Isosterism and Molecular Modification in Drug Design; Chemical Society Reviews; 1979; vol. 8, Iss. 4; pp. 563-580;.

(Continued)

*Primary Examiner*—Charanjit S. Aulakh
(74) *Attorney, Agent, or Firm*—Robert J. Smith

(57) ABSTRACT

The present invention relates to compounds of formula (I) as defined herein and salts or solvates thereof. Processes for preparing these compounds and pharmaceutical formulations containing them are also disclosed, as well as methods for the prophylaxis of treatment of a clinical condition using such compounds.

25 Claims, No Drawings

OTHER PUBLICATIONS

Iakovidis, D. et al.; Synthesis and beta-andrenoceptor agonist properties of (+/-)-1-(3', 4'-dihydroxyphenoxy)-3-(3", 4"-dimethooxyphenyl)ethylamino-2-propanol hydrochloride, (+/-)-RO363.HCI,and the (2S)-(-)-isomer; European Journal of Medicinal Chemistry; 1999; vol. 34, No. 6; pp. 539-548;.

Fuji et al.; Novelphosphodiesterase 4 inhibitor T-440 reverse and prevents human bronchial contraction induced by allergen.; Journal of Pharmacology and Experimental Therapeutics; 1998; vol. 284, No. 1; pp. 162-169;.

Landells, et al.; Oral administration of the phosphodiesterase (PDE)4 inhibitor, V11294 inhibits ex-vivo agonist-induced-cell activation.; European Respiratory Journal (/annu Cong Eur Resp Soc, Geneva); 1998; vol. 12, Suppl. 28; Abst P2393;.

McHale, M.M.et al.; Expression of Human recombinant cAMP Phosphodiesterase Isozyme IV Reverses Growth Arrest Phenotypes in Phosphodiesterase-Deficient Yeast; Molecular Pharmacology; 1991; vol. 39; pp. 109-113.

Nicholson, C. D, et al.; Differential modulation of tissue function and therapeutic potential of selective inhibitors of cyclic nucleotide phosphodiesterase isoenzymes; Trends in Pharmacological Sciences; 1991; vol. 12; pp. 19-27;.

Torphy, T.J., et al.; Role of Cyclic Nucleotide Phosphodiesterase Isozymes in Intact Canine Trachealis; Molecular Pharmacology; 1991; vol. 39; pp. 376-384;.

ARYLETHANOLAMINE $\beta_2$-ADRENORECEPTOR AGONIST COMPOUNDS

CROSS-REFERENCE TO RELATED APPLICATIONS

This application is filed under 35 U.S.C. § 371 as the United States National Phase Application of International Application No. PCT/EP2003/008264 filed Jul. 24, 2003 claiming priority from GB Application No. 0217225.2 filed Jul. 25, 2002.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the maximum duration of action is 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

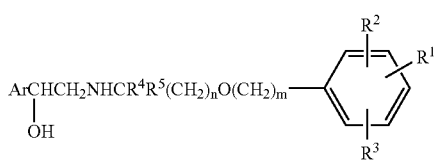

(I)

or a salt, solvate, or physiologically functional derivative thereof, wherein:

n is an integer of from 2 to 8;

m is an integer of from 3 to 11, preferably from 3 to 7, with the proviso that the sum of n+m is from 5 to 19, preferably 5 to 12;

$R^1$ is hydrogen or —$XSO_2NR^6R^7$;

wherein X is —$(CH_2)_p$— or $C_{2-6}$ alkenylene;

p is an integer from 0 to 6, preferably 0 to 4;

$R^6$ and $R^7$ are independently selected from hydrogen, $C_{1-6}$alkyl, $C_{3-7}$cycloalkyl, $CONR^8R^9$, phenyl and phenyl ($C_{1-4}$alkyl)-, or $R^6$ and $R^7$, together with the nitrogen atom to which they are bonded, form a 5-, 6- or 7-membered nitrogen—containing ring;

and $R^6$ and $R^7$ are each independently optionally substituted by 1 or 2 groups independently selected from halo, $C_{1-6}$alkyl, $C_{1-6}$alkoxy, hydroxy-substituted $C_{1-6}$alkoxy, $C_{1-6}$haloalkyl, $CO_2R^8$, $SO_2R^8R^9$, —$CONR^8R^9$, —$NR^8C(O)R^9$ or a 5-, 6- or 7-membered heterocyclic ring;

$R^8$ and $R^9$ are independently selected from hydrogen, $C_{1-6}$alkyl, $C_{3-7}$cycloalkyl, phenyl and phenyl($C_{1-6}$alkyl)-;

$R^2$ and $R^3$ are independently selected from hydrogen, $C_{1-6}$alkyl, $C_{1-6}$alkoxy, halo, phenyl and $C_{1-6}$haloalkyl;

$R^4$ and $R^5$ are independently selected from hydrogen and $C_{1-4}$ alkyl with the proviso that the total number of carbon atoms in $R^4$ and $R^5$ is not more than 4, and Ar is a group selected from

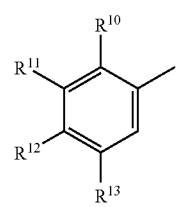

(a)

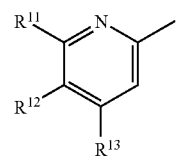

(b)

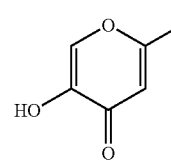 and (c)

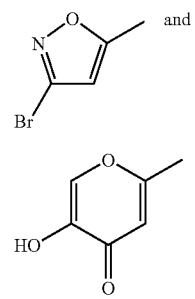

(d)

wherein $R^{11}$ represents hydrogen, halogen, —$(CH_2)_qOR^{14}$, —$NR^{14}C(O)R^{15}$, —$NR^{14}SO_2R^{15}$, —$SO_2NR^{14}R^{15}$, —$NR^{14}R^{15}$, —$OC(O)R^{16}$ or $OC(O)NR^{14}R^{15}$, and $R^{10}$ represents hydrogen, halogen or $C_{1-4}$alkyl;

or $R^{11}$ represents —$NHR^{17}$ and $R^{10}$ and —$NHR^{17}$ together form a 5- or 6-membered heterocyclic ring;

$R^{12}$ represents hydrogen, halogen, —$OR^{14}$ or —$NR^{14}R^{15}$;

$R^{13}$ represents hydrogen, halogen, haloC$_{1-4}$alkyl, —$OR^{14}$, —$NR^{14}R^{15}OC(O)R^{16}$ or $OC(O)NR^{14}R^{15}$;

$R^{14}$ and $R^{15}$ each independently represents hydrogen or $C_{1-4}$ alkyl, or in the groups —$NR^{14}R^{15}$, —$SO_2NR^{14}R^{15}$ and —$OC(O)NR^{14}R^{15}$, $R^{14}$ and $R^{15}$ independently represent hydrogen or $C_{1-4}$ alkyl or together with the nitrogen atom to which they are attached form a 5-, 6- or 7-membered nitrogen-containing ring, $R^{16}$ represents an aryl (eg phenyl or naphthyl) group which may be unsubstituted or substituted by one or more substituents selected from halogen, $C_{1-4}$ alkyl, hydroxy, $C_{1-4}$ alkoxy or halo $C_{1-4}$ alkyl; and q is zero or an integer from 1 to 4;

provided that when $R^1$ is hydrogen

Ar is not a group (a) wherein;

$R^{11}$ is —$(CH_2)_qOR^{14}$, q is zero or 1 and $R^{12}$ is $OR^{14}$, or $R^{11}$ is —$(CH_2)_qOR^{14}$, q is zero and $R^{13}$ is $OR^{14}$, or $R^{11}$ is —$NR^{14}SO_2R^{15}$ or $NR^{14}COR^{15}$ and $R^{12}$ is $OR^{14}$, or $R^{11}$ and $R^{13}$ both represent halogen and $R^{12}$ is $NR^{14}R^{15}$;

Ar is not a group (b) wherein $R^{11}$ is —$(CH_2)_qOR^{14}$ and $R^{12}$ is $OR^{14}$;

Ar is not a group (c),
and when $R^1$ is $XSO_2NR^6R^7$, Ar is not a group (a) wherein $R^{11}$ is $(CH_2)_qOR^{14}$ or $NR^{14}COR^{15}$, and $R^{12}$ is $OR^{14}$.

In a particular embodiment of this invention, in the group Ar, $R^{11}$ represents halogen, —$(CH_2)_qOR^{14}$, —$NR^{14}C(O)R^{15}$, —$NR^{14}SO_2R^{15}$, —$SO_2NR^{14}R^{15}$, —$NR^{14}R^{15}$, —$OC(O)R^{16}$ or $OC(O)NR^{14}R^{15}$, and $R^{10}$ represents hydrogen,
or $R^{11}$ represents —$NHR^{17}$ and $R^{10}$ and —$NHR^{17}$ together form a 5- or 6-membered heterocyclic ring;

and
$R^{13}$ represents hydrogen, halogen, halo$C_{1-4}$ alkyl, —$OR^{14}$, or —$NR^{14}R^{15}$;

and all other substituents are as defined above.

In the compounds of formula (I), the group $R^1$ is preferably attached to the meta-position relative to the —O—$(CH_2)_m$ link.

$R^1$ preferably represents $SO_2NR^6R^7$ wherein $R^6$ and $R^7$ are independently selected from hydrogen and $C_{1-6}$alkyl. More preferably $R^1$ is $SO_2NH_2$.

$R^4$ and $R^5$ are preferably independently selected from hydrogen and methyl, more preferably $R^4$ and $R^5$ are both hydrogen.

In the compounds of formula (I) $R^2$ and $R^3$ preferably each represent hydrogen.

The integer n is suitably 4, 5 or 6 and m is suitably 3, 4, 5 or 6. Preferably n is 5 or 6 and m is 3 or 4 such that m+n is 8, 9 or 10, preferably 9.

In the compounds of formula (I) the group Ar is preferably selected from groups (a) and (b) above. In said groups (a) and (b), when $R^{11}$ represents halogen this is preferably chlorine or fluorine, especially fluorine. $R^{14}$ and $R^{15}$ preferably each independently represent hydrogen or methyl. $R^{16}$ preferably represents substituted phenyl. The integer q preferably represents zero or 1. Thus for example —$(CH_2)_qOR^{14}$ preferably represents OH or —$CH_2OH$;
$NR^{14}C(O)R^{15}$ preferably represents —NHC(O)H;
—$SO_2NR^{14}R^{15}$ preferably represents —$SO_2NH_2$ or $SO_2NHCH_3$;
$NR^{14}R^{15}$ preferably represents —$NH_2$;
—$OC(O)R^{16}$ preferably represents substituted benzoyloxy eg. $OC(O)$—$C_6H_4$—$(p$—$CH_3)$; and
—$OC(O)NR^{14}R^{15}$ preferably represents $OC(O)N(CH_3)_2$.

When $R^{11}$ represents $NHR^{17}$ and together with $R^{10}$ forms a 5- or 6-membered heterocyclic ring —$NHR^{17}$—$R^{10}$— preferably represents a group:
—NH—CO—$R^{18}$ where $R^{18}$ is an alkylene, and alkenylene or alkenyloxy group,
—NH—$SO_2R^{19}$ where $R^{19}$ is an alkenyloxy group,
—NH—$R^{20}$ ($COOR^{21}$) where $R^{19}$ is an alkylene or alkenylene group and $R^{20}$ is $C_{1-4}$ alkyl, or
—NH—CO—CH— or NH—CO—S, wherein said alkylene, and alkenylene groups and moieties contain 1 or 2 carbon atoms.

Particularly preferred groups (a) and (b) may be selected from the following groups (i) to (xx):

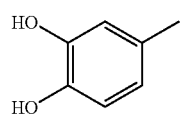
(i)

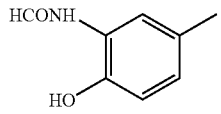
(ii)

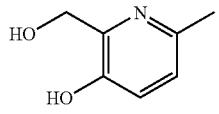
(iii)

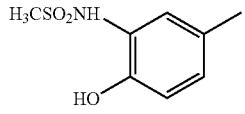
(iv)

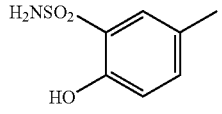
(v)

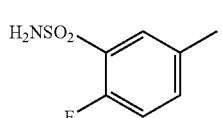
(vi)

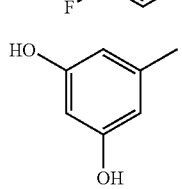
(vii)

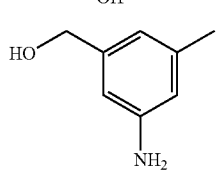
(viii)

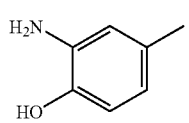
(ix)

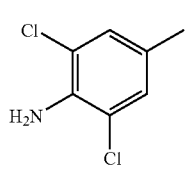
(x)

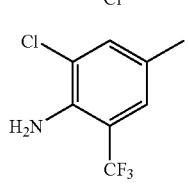
(xi)

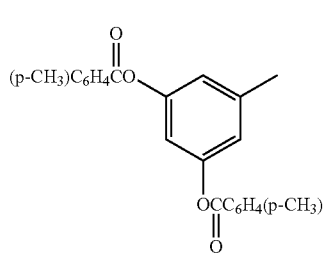
(xii)

-continued

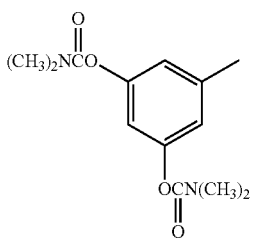 (xiii)

 (xiv)

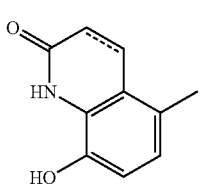 (xv)

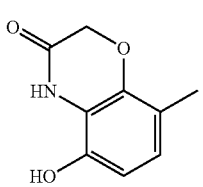 (xvi)

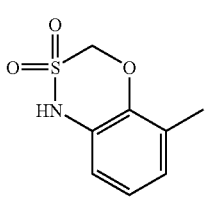 (xvii)

 (xviii)

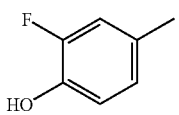 (xix)

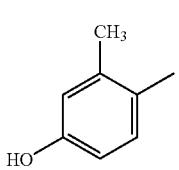 (xx)

wherein the dotted line in (xv) and (xviii) denotes an optional double bond.

It will be appreciated that when $R^1$ represents hydrogen, Ar is not a group having the structure (i), (iii), (iv), (vii) or (x).

Furthermore, when $R^1$ represents a group —$XSO_2NR^6R^7$, Ar is not a group having the structure (ii).

Thus, when $R^1$ is hydrogen, Ar is preferably selected from a group of structure (ii), (v), (vi), (viii), (ix), (xi), (xii), (xiii), (xiv), (xv), (xvi), (xvii) and (xviii).

Most preferably when $R^1$ is hydrogen Ar is selected from a group of structure (xiv), (xv), (xvi) and (xvii).

When $R^1$ is $XSO_2NR^6R^7$, Ar is preferably selected from a group of structure (iii), (iv), (xiv), (xv), (xvi) and (xix).

It is to be understood that the present invention covers all combinations of particular and preferred groups described hereinabove.

Preferred compounds of the invention include:
8-Hydroxy-5-((1R)-1-hydroxy-2-{[6-(4-phenylbutoxy)hexyl]amino}ethyl)quinolin-2(1H)-one;
3-{4-[(6-{[(2R)-2-Hydroxy-2-(8-hydroxy-2-oxo-1,2-dihydroquinolin-5-yl)ethyl]amino}hexyl)oxy]butyl}benzenesulfonamide;
5-Hydroxy-8-(1-hydroxy-2-{[6-(4-phenylbutoxy)hexyl]amino}ethyl)-2H-1,4-benzoxazin-3(4H)-one;
3-{4-[(6-{[2-hydroxy-2-(5-hydroxy-3-oxo-3,4-dihydro-2H-1,4-benzoxazin-8-yl)ethyl]amino}hexyl)oxy]butyl}benzenesulfonamide;
4-Hydroxy-7-((1R)-1-hydroxy-2-{[6-(4-phenylbutoxy)hexyl]amino}ethyl)-1,3-benzothiazol-2(3H)-one;
4-Hydroxy-7-(1-hydroxy-2-{[6-(4-phenylbutoxy)hexyl]amino}ethyl)-1,3-benzothiazol-2(3H)-one;
3-{4-[(6-{[(2R)-2-(3-Fluoro-4-hydroxyphenyl)-2-hydroxyethyl]amino}hexyl)oxy]butyl}benzenesulfonamide;
3-(4-{[6-({2-Hydroxy-2-[5-hydroxy-6-(hydroxymethyl)pyridin-2-yl]ethyl}amino)hexyl]oxy}butyl)benzenesulfonamide;
3-[4-({6-[((2R)-2-Hydroxy-2-{4-hydroxy-3-[(methylsulfonyl)amino]phenyl}ethyl)amino]hexyl}oxy)butyl]benzenesulfonamide;
3-{3-[(7-{[(2R)-2-(3-Fluoro-4-hydroxyphenyl)-2-hydroxyethyl]amino}heptyl)oxy]propyl}benzenesulfonamide;
3-(3-{[7-({2-Hydroxy-2-[5-hydroxy-6-(hydroxymethyl)pyridin-2-yl]ethyl}amino)heptyl]oxy}propyl)benzenesulfonamide;
3-[3-({7-[((2R)-2-Hydroxy-2-{4-hydroxy-3-[(methylsulfonyl)amino]phenyl}ethyl)amino]heptyl}oxy)propyl]benzenesulfonamide;
3-{3-[(7-{[(2R)-2-Hydroxy-2-(8-hydroxy-2-oxo-1,2-dihydroquinolin-5-yl)ethyl]amino}heptyl)oxy]propyl}benzenesulfonamide;
3-(3-{[7-({(2R)-2-[3-(Formylamino)-4-hydroxyphenyl]-2-hydroxyethyl}amino)heptyl]oxy}propyl)benzenesulfonamide;

and salts, solvates and physiologically functional derivatives thereof.

The compounds of formula (I) include an asymmetric centre, namely the carbon atom of the

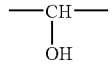

group. The present invention includes both (S) and (R) enantiomers either in substantially pure form or admixed in any proportions. Preferably, the compounds of the invention are in the form of the (R) enantiomers.

Similarly, where $R^4$ and $R^5$ are different groups, the carbon atom to which they are attached is an asymmetric centre and the present invention includes both (S) and (R) enantiomers at this centre either in substantially pure form or admixed in any proportions.

Thus the compounds of formula (I) include all enantiomers and diastereoisomers as well as mixtures thereof in any proportions.

Salts and solvates of compounds of formula (I) which are suitable for use in medicine are those wherein the counterion or associated solvent is pharmaceutically acceptable.

However, salts and solvates having non-pharmaceutically acceptable counterions or associated solvents are within the scope of the present invention, for example, for use as intermediates in the preparation of other compounds of formula (I) and their pharmaceutically acceptable salts, solvates, and physiologically functional derivatives.

By the term "physiologically functional derivative" is meant a chemical derivative of a compound of formula (I) having the same physiological function as the free compound of formula (I), for example, by being convertible in the body thereto. According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Pharmaceutically acceptable esters of the compounds of formula (I) may have a hydroxyl group converted to a $C_{1-6}$alkyl, aryl, aryl $C_{1-6}$ alkyl, or amino acid ester.

As mentioned above, the compounds of formula (I) are selective $\beta_2$-adrenoreceptor agonists as demonstrated using functional or reporter gene readout from cell lines transfected with human beta-adrenoreceptors as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. As such, compounds of the invention may be suitable for once-daily administration.

Therefore, compounds of formula (I) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease.

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I), or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I), or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated.

In particular, there is provided a compound of formula (I), or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I), or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I), or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease. In a further aspect, there is provided a compound of formula (I), or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I), or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1 mg per day.

While it is possible for the compound of formula (I), or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I), or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 20 μg-10 mg of the compound of formula (I) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic add or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-35-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$ ratios is set out in U.S. Pat. No. 5,998,428, which is incorporated herein in full by reference as though set out herein. See also PCT application WO 00/57599 for another description of said assay.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other Compounds of Interest Include:

Compounds set out in U.S. Pat. No. 5,552,438 issued 03 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6] naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide— CAS4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt— CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

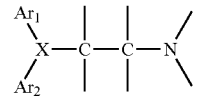

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a corticosteroid.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a corticosteroid.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I), or a salt, solvate, or physiologically functional derivative thereof which comprises a process (a), (b), (c) or (d) as defined below followed by the following steps in any order (i) optional removal of any protecting groups;
(ii) optional separation of an enantiomer from a mixture of enantiomers;
(iii) optional conversion of the product to a corresponding salt, solvate,
(iv) optional conversion of a group $R^1$, $R^2$ and/or $R^3$ to another group $R^1$, $R^2$ and/or $R^3$, or physiologically functional derivative thereof.

In the following description of synthetic routes, $R^1$, $R^2$, $R^3$, $R^4$, $R^5$, m and n are as defined for formula (I) and $R^{25}$, $R^{26}$, and $R^{27}$ are as defined for formula (II) below unless indicated otherwise.

In one general process (a), a compound of formula (I), may be obtained by deprotection of a protected intermediate, for example of formula (II):

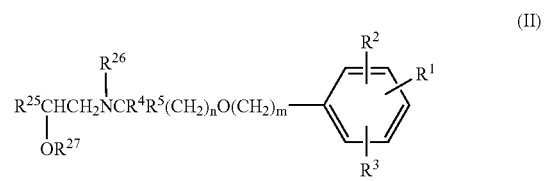

or a salt or solvate thereof, wherein $R^1$, $R^2$, $R^3$, $R^4$, $R^5$, m and n are as defined for the compounds of formula (I), and $R^{25}$ represents an optionally protected form of Ar and $R^{26}$ and $R^{27}$ each independently represents either hydrogen or a protecting group, provided that the compound of formula (II) contains at least one protecting group.

Protected forms of the preferred groups Ar may be selected from:

(ia)

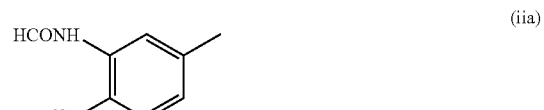

(iia)

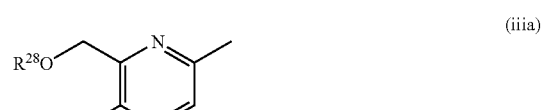

(iiia)

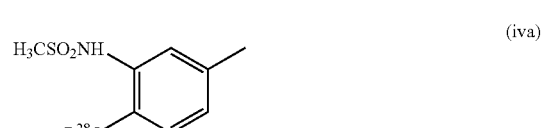

(iva)

(va)

(via)

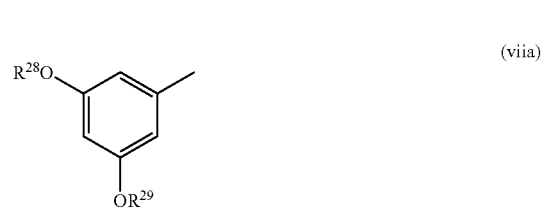

(viia)

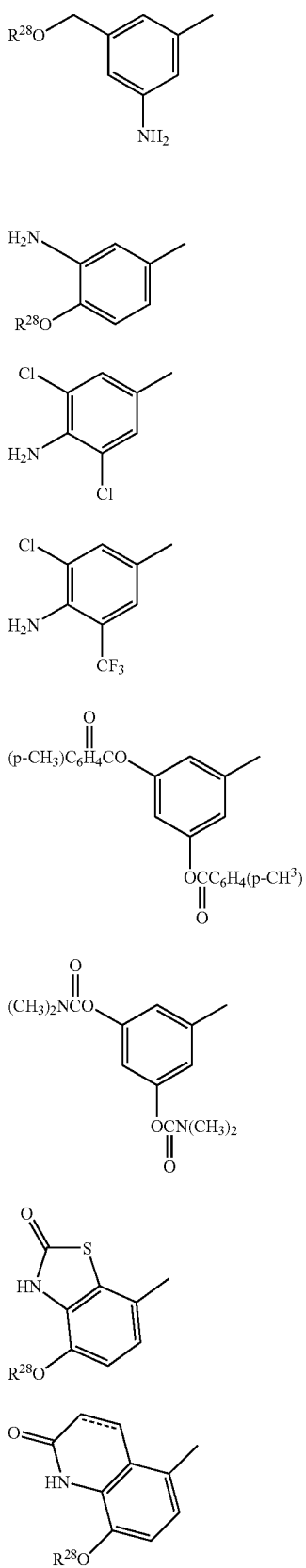

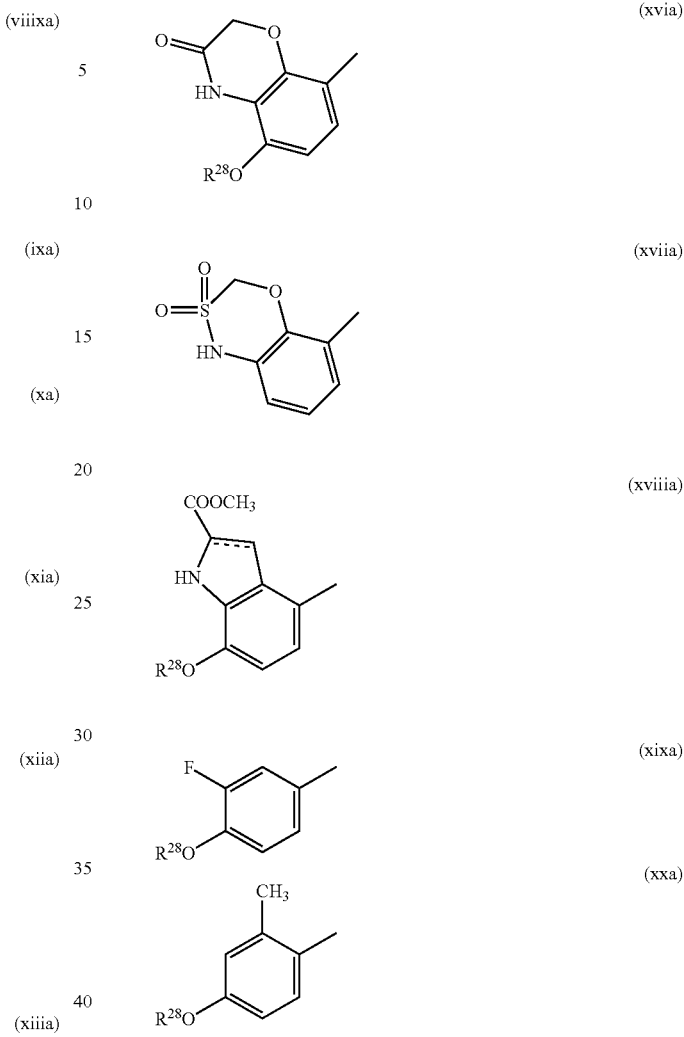

wherein $R^{28}$ and $R^{29}$ are each independently either hydrogen or a protecting group provided that at least one of $R^{28}$ and $R^{29}$ is a protecting group; and the dotted line in (xviiia) and (xxa) denotes an optional double bond.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^{28}$ and $R^{29}$ are esters such as acetate ester, aralkyl groups such as benzyl, diphenylmethyl, or triphenylmethyl, and tetrahydropyranyl. Examples of suitable amino protecting groups represented by $R^{26}$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as —CH(OR$^{27}$) using, for example, a trialkylsilyl group such as triethylsilyl. A person skilled in the art will also appreciate other orthogonal protection strategies, available by conventional means as described in Theodora W Greene and Peter G M Wuts (see above).

The deprotection to yield a compound of formula (I), may be effected using conventional techniques. Thus, for example, when $R^{28}$, $R^{29}$, and/or $R^{26}$ is an aralkyl group, this may be cleaved by hydrogenolysis in the presence of a metal catalyst (e.g. palladium on charcoal).

When $R^{28}$ and/or $R^{29}$ is tetrahydropyranyl this may be cleaved by hydrolysis under acidic conditions. Acyl groups represented by $R^{26}$ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene and Peter G M Wuts (see above).

In a particular embodiment of process (a), when $R^{25}$ represents a group (iiia) $R^{28}$ and $R^{29}$ may together represent a protecting group as in the compound of formula (III):

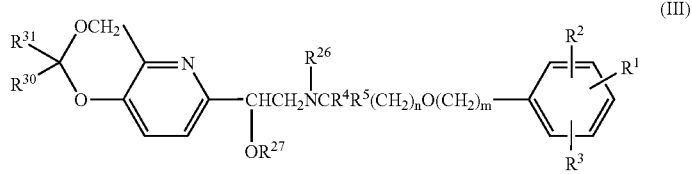

(III)

or a salt or solvate thereof, wherein $R^1$, $R^2$, $R^3$, $R^4$, $R^5$, $R^{26}$, $R^{27}$, m and n are as defined for the compound of formula (II), and $R^{30}$ and $R^{31}$ are independently selected from hydrogen, $C_{1-6}$alkyl, or aryl or $R^{30}$ and $R^{31}$ together form a carbocyclic ring eg. containing from 5 to 7 carbon atoms.

The compound of formula (III) may be converted to a compound of formula (I), by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

It will be appreciated that the protecting groups $R^{28}$, $R^{29}$, $R^{26}$ and $R^{27}$ (including the cyclised protecting group formed by $R^{30}$ and $R^{31}$ as depicted in formula (III) may be removed in a single step or sequentially. The precise order in which protecting groups are removed will in part depend upon the nature of said groups and will be readily apparent to the skilled worker. Preferably, when $R^{30}$ and $R^{31}$ together form a protecting group as in formula (III) this protecting group is removed together with any protecting group on the CH(OH) moiety, followed by removal of $R^{26}$.

Compounds of formulae (II) and (III) wherein $R^{26}$ is hydrogen may be prepared from the corresponding compound of formula (IV).

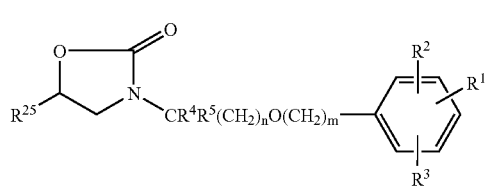

(IV)

or a salt or solvate thereof, wherein $R^1$, $R^2$, $R^3$, $R^4$, $R^5$, $R^{25}$, m and n are as defined for the compound of formula (II) or (III).

The conversion of a compound of formula (IV) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

Compounds of formula (IV) may be prepared by reacting a compound of formula (V):

(V)

with a compound of formula (VI):

(VI)

LCR$^4$R$^5$(CH$_2$)$_n$O(CH$_2$)$_m$—

Wherein L is a leaving group such as halo (typically chloro, bromo or iodo) or a sulphonate (typically methanesulphonate) and $R^1$, $R^2$, $R^3$, $R^4$, $R^5$, n and m are as defined for compounds of formula (I).

The coupling of a compound of formula (V) with a compound of formula (VI) may be effected in the presence of a base, such as a metal hydride, for example sodium hydride, or an inorganic base such as cesium carbonate, in an aprotic solvent, for example N,N-dimethylformamide.

Compounds of formula (V) may be prepared by ring closure of a compound of formula (VII):

(VII)

wherein $R^{25}$ is as hereinbefore defined and $R^{33}$ is $C_{1-6}$alkyl, for example tert-butyl, or aryl, for example phenyl. The ring closure may be effected by treatment with a base, such as a metal hydride, for example sodium hydride, in the presence of an aprotic solvent, for example, N,N-dimethylformamide.

The compound of formula (VII) may be prepared from the corresponding halide of formula (VIII):

(VIII)

wherein $R^{25}$ and Y are as hereinbefore defined, by reaction with a protected amine $HN(COOR^{33})_2$, wherein $R^{33}$ is as defined for the compound of formula (VII), in the presence of an inorganic base such as cesium carbonate, followed by selective removal of one of the $COOR^{33}$ groups, for example by treatment with an acid such as trifluoroacetic acid, and subsequent reduction of the keto function by any suitable method, for example by treatment with borane, in the presence of a chiral catalyst, such as CBS-oxazaborolidine, in a suitable solvent such as tetrahydrofuran.

A compound of formula (VI) may be prepared by coupling a compound of formula (IX):

$$LCR^4R^5(CH_2)_nO(CH_2)_{m-2}C\!\!\equiv\!\!CH \tag{IX}$$

wherein L is a leaving group as defined for formula (VI); with a compound of formula (X):

(X)

Wherein $L^1$ is a leaving group as hereinbefore defined for L and $R^1$, $R^2$, $R^3$, are as hereinbefore defined, followed by reduction.

The coupling of a compound of formula (IX) with a compound of formula (X) is conveniently effected in the presence of a catalyst system such as bis(triphenyphosphine)palladium dichloride with an organic base such as a trialkylamine, for example diisopropylethylamine, in a suitable solvent for example acetonitrile or dimethylformamide or using the base as solvent. The resulting alkyne may then be reduced, either with or without being isolated to form the desired saturated alcohol. The reduction may be effected by any suitable method such a hydrogenation in the presence of a catalyst, for example palladium/charcoal or platinum oxide.

Compounds of formula (X) are commercially available or may be prepared by methods well known to the person skilled in the art.

A compound of formula (IX) may be prepared by reacting a compound of formula (XI):

$$HO(CH_2)_{m-2}C\!\!\equiv\!\!CH \tag{XI}$$

Wherein m is as defined for formula (I) with a dihaloalkane of formula (XII):

$$Y^1CR^4R^5(CH_2)_nY^2 \tag{XII}$$

wherein $R^4$, $R^5$ and n are as hereinbefore defined and $Y^1$ and $Y^2$ each represent halo.

The reaction of compounds (XI) and (XII) is typically effected in the presence of an inorganic base, such as sodium hydroxide under phase transfer conditions in the presence of a tetra-alkylammonium salt, eg. tetrabutylammonium bromide.

Compounds of formulae (XI) and (XII) are available commercially or can be prepared by standard methods.

Alternatively, compounds of formula (II) and (III) wherein $R^{26}$ is either hydrogen or a protecting group may be prepared by any of the processes described hereinafter.

In a further process (b) a compound of formula (I) may be obtained by reacting a compound of formula (XIII):

(XIII)

Wherein Ar is as defined above, with a compound of formula (VI):

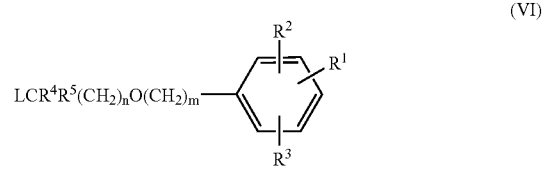

(VI)

Wherein L is a leaving group such as halo (typically chloro, bromo or iodo) or a sulphonate (typically methanesulphonate) and $R^1$, $R^2$, $R^3$, $R^4$, $R^5$, n and m are as defined for compounds of formula (I).

The reaction of compounds of formula (XIII) and (VI) is optionally effected in the presence of an organic base, such as a trialkylamine, for example triethylamine, and in a suitable solvent, for example an amide such as DMF.

Compounds of formula (XIII) may be prepared by methods well known in the art. Thus for example they may be readily prepared by a person skilled in the art, from the corresponding halide of formula (XIV):

(XIV)

wherein Ar is as hereinbefore defined and Y is halo eg. bromo.

The conversion of a compound of formula (XIV) to a compound of formula (XIII) may be effected by reaction with sodium azide in a suitable solvent, for example N,N-dimethylformamide, to give the corresponding compound wherein Y denotes $N_3$. The carbonyl group may then be reduced to the corresponding alcohol by any suitable method, for example by treatment with borane, in the presence of a chiral catalyst, such as (R)-tetrahydro-1-methyl-3,3-diphenyl-1H,3H-pyrrolo[1,2-c][1,3,2]oxazaborole, in a suitable solvent such as tetrahydrofuran. The azide group may be reduced to the corresponding amine group by any suitable method, for example by catalytic hydrogenation in the presence of a catalyst such as palladium/charcoal or platinum oxide.

Further details concerning preparation of compounds (XIII) wherein Ar is a group (iv) in DE3524990; concerning the preparation of compounds (XIII) wherein Ar is a group (i), (vii), and (xv) in EP-A-162576; concerning the preparation of compounds (XIII) wherein Ar is a group (iii) in EP-A-22054; concerning the preparation of compounds (XIII) wherein Ar is a group (x) in GB2165542 and concerning the preparation of compounds (XIII) wherein Ar is a group (c) in GB2230523.

Compounds of formula (XIV) are known compounds or may readily be prepared by those skilled in the art using known methods.

In a further process (c) a compound of formula (I), may be prepared by reacting a compound of formula (XV):

(XV)

wherein L is a leaving group as hereinbefore defined, with an amine of formula (XVI):

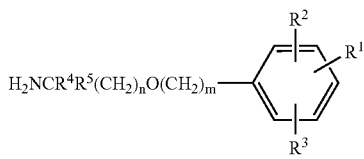
(XVI)

The reaction may be effected using conventional conditions for such displacement reactions.

Compounds of formula (XV) may be prepared by methods known in the art.

Thus for example, compounds (XV) wherein Ar is a group (xv) may be prepared as described in EP-A-147719.

Compounds of formula (XVI) may be prepared by reacting a compound of formula (VI) with an amine $R^{26}NH_2$, followed by removal of the protecting group $R^{26}$.

According to a further process (d) compounds of formula (I) wherein one of $R^4$ and $R^5$ represents hydrogen may be prepared by;

(i) reacting a compound of formula (XIII):

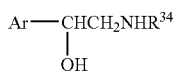
(XIII)

Wherein Ar is as hereinbefore defined and $R^{34}$ represents hydrogen or a chiral auxiliary, with a compound of formula (XVII):

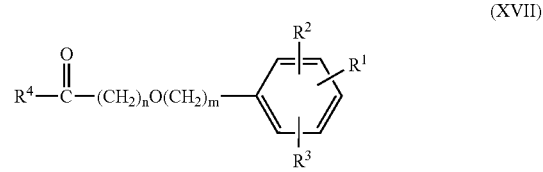
(XVII)

wherein $R^1$, $R^2$, $R^3$, $R^4$, n and m are as hereinbefore defined; followed where necessary by removal of the chiral auxiliary $R^{34}$;

or (ii) reacting a compound of formula (XVIII):

(XVIII)

wherein Ar is as hereinbefore defined; with an amine of formula (XVI):

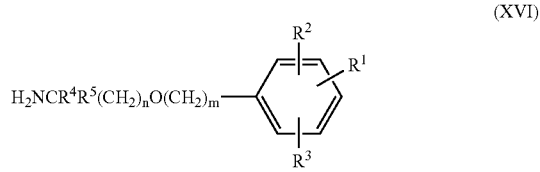
(XVI)

as hereinbefore defined, under conditions suitable to effect reductive amination, for example in the presence of a reducing agent such as a borohydride, trypically tetramethylammonium (triacetoxy)borohydride.

When process (di) involves use of a chiral auxiliary this is preferably the S-isomer and/or the R-isomer of phenyl glycinol. The reaction may be effected as described in International Application Number WO/0196278.

A compound of formula (XVII) may be prepared by methods known in the art, for example via a compound of formula (VI) as hereinbefore defined.

A compound of formula (XVIII) may also be prepared from a corresponding alcohol, which may itself be obtained from a compound of formula (XV) as hereinbefore defined, using standard methods well known to those skilled in the art.

It will be appreciated that in any of the routes (a) to (d) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. It will also be appreciated that in the processes (b), (c) and (d) appropriate protecting groups may be employed if necessary and/or desired and removed at any suitable stage of the synthesis, eg. in the last stage, as described in process (a).

The enantiomeric compounds of the invention may be obtained (i) by separation of the components of the corresponding racemic mixture, for example, by means of a chiral chromatography column, enzymic resolution methods, or preparing and separating suitable diastereoisomers, or (ii) by direct synthesis from the appropriate chiral intermediates by the methods described above.

Optional conversions of a compound of formula (I), to a corresponding salt may conveniently be effected by reaction with the appropriate acid or base. Optional conversion of a compound of formula (I), to a corresponding solvate or physiologically functional derivative may be effected by methods known to those skilled in the art.

According to a further aspect, the present invention provides novel intermediates for the preparation of compounds of formula (I), for example:

compounds of formula

For a better understanding of the invention, the following Examples are given by way of illustration.

SYNTHETIC EXAMPLES

Throughout the examples, the following abbreviations are used:
LC: Liquid Chromatography
LCMS: Liquid Chromatography Mass Spectrometry
HPLC: High Performance Liquid Chromatography
RT: retention time
DCM: dichloromethane
IMS: industrial methylated spirits
EtOAc: ethyl acetate
EtOH: ethanol
DMAP: N,N-Dimethylaminopyridine
DMF: N,N-Dimethylformamide
MeOH: methanol
THF: tetrahydrofuran
IMS: Industrial methylated spirits
h: hour(s)
min: minute(s)

All temperatures are given in degrees celcius.

Flash silica gel refers to Merck Art No. 9385; silica gel refers to Merck Art No. 7734

Biotage refers to prepacked silica gel cartridges containing KP-Sil run on flash 12i chromatography module.

Solid Phase Extraction (SPE) columns are pre-packed cartridges used in parallel purifications, normally under vacuum. These are commercially available from Varian.

SCX cartridges are Ion Exchange SPE columns where the stationary phase is polymeric benzene sulfonic acid. These are used to isolate amines.

LC was conducted on a Luna C18(2) column (5 cm×2.0 mm ID) eluting with 0.05% v/v trifluoroacetic acid in water (solvent A) and 0.05% v/v trifluoroacetic acid in acetonitrile (solvent B) using the following elution gradient 0.00-8.00 min 0% B, 8.00-8.01 min 95% B, 8.01-10.00 min 0% B at a flow rate of 1.0 ml/min with a column temperature of 40° C.

LCMS was conducted on a Supelcosil LCABZ+PLUS column (3.3 cm×4.6 mm ID) eluting with 0.1% $HCO_2H$ and 0.01M ammonium acetate in water (solvent A) and 0.05% $HCO_2H$ 5% water in acetonitrile (solvent B), using the following elution gradient 0.0-7 min 0% B, 0.7-4.2 min 100% B, 4.2-5.3 min 0% B, 5.3-5.5 min 0% B at a flow rate of 3 mL/min. The mass spectra were recorded on a Fisons VG Plafform spectrometer using electrospray positive and negative mode (ES+ve and ES−ve).

Preparative mass directed HPLC was conducted on a Waters FractionLynx system comprising of a Waters 600 pump with extended pump heads, Waters 2700 autosampler, Waters 996 diode array and Gilson 202 fraction collector on a 10 cm×2.54 cm ID ABZ+column, eluting with 0.1% formic acid in water (solvent A) and 0.1% formic acid in acetonitrile (solvent B), using the following elution gradient: 0.0-1.0 min 15% B, 1.0-10.0 min 55% B, 10.0-14.5 min 99% B, 14.5-14.9 min 99% B, 14.9-15.0 min 15% B at a flow rate of 20 ml/min and detecting at 200-320 nm at room temperature. Mass spectra were recorded on Micromass ZMD mass spectrometer using electrospray positive and negative mode, alternate scans. The software used was MassLynx 3.5 with OpenLynx and FractionLynx options.

EXAMPLE 1

8-Hydroxy-5-((1R)-1-hydroxy-2-{[6-(4-phenylbutoxy)hexyl]amino}ethyl)quinolin-2(1H)-one acetate (i) 8-(Benzyloxy)-5-[(1R)-2-bromo-1-hydroxyethyl]quinolin-2(1H)-one A solution of [(R)-tetrahydro-1-methyl-3,3-diphenyl-1H, 3H-pyrrolo[1,2-c] [1,3,2]-oxazaborole] (1M, 424 μL) in THF (2 ml) was added to borane dimethylsulfide complex (2M, 212.7 μl) in THF (15 ml) and stirred at 0° C. for 10 min. The reaction mixture was cooled to −10° C. and treated with a solution of 8-benzyloxy-5-bromoacetylcarbostyril (EP 147719A2) (791 mg) in THF (16 ml) over 20 min. Further borane dimethylsulfide complex (1.28 ml) was added over 4 h at 0° C. The reaction mixture was stirred for a further hour at 0° C. prior to quenching with methanol and 1N HCl(aq). The reaction mixture was partitioned between water and ethyl acetate. The organic phase was dried and concentrated in vacuo. The residue was triturated with hexane-ethyl acetate to afford the title compound (700 mg). Rf (EtOAc) 0.47

(ii) 8-(Benzyloxy)-5-[(1R)-2-bromo-1-(tetrahydro-2H-pyran-2-yloxy)ethyl]quinolin-2(1H)-one A suspension of 8-(benzyloxy)-5-[(1R)-2-bromo-1-hydroxyethyl]quinolin-2(1H)-one (100 mg) and pyridinium tosylate (14 mg) in dry DCM (2 ml) was treated with 2,3-dihydropyran (61.2 μl) and stirred at 22° C. for 18 h. The reaction mixture was concentrated in vacuo and purified by chromatography (Hexane-EtOAc 2:1, biotage) to give the title compound (77 mg). Rf [EtOAc-Hexane (1:1)] 0.54

(iii) 8-(Benzyloxy)-5-[(1R)-2-{benzyl[6-(4-phenylbutoxy)hexyl]amino}-1-(tetrahydro-2H-pyran-2-yloxy)ethyl]quinolin-2(1H)-one 8-(Benzyloxy)-5-[(1R)-2-bromo-1-(tetrahydro-2H-pyran-2-yloxy)ethyl]quinolin-2(1H)-one (100 mg), N-benzyl-6-(4-phenylbutoxy)hexan-1-amine (*Tetrahedron Letters*. 1994, 35, 9375) (112 mg) and diisopropylethylamine (77 μl) were heated in a reacti-vial at 120° C. for 4 h prior to cooling to room temperature. The mixture was purified by chromatography (Hexane-EtOAc 2:1, biotage) afforded the title compound (85 mg). LCMS RT=3.46 min (iv) 8-(Benzyloxy)-5-((1R)-2-{benzyl[6-(4-phenylbutoxy)hexyl]amino}-1-hydroxyethyl)quinolin-2 (1H)-one A solution of 8-(benzyloxy)-5-[(1R)-2-{benzyl[6-(4-phenylbutoxy)hexyl]amino}-1-(tetrahydro-2H-pyran-2-yloxy) ethyl]quinolin-2(1H)-one (80 mg) in acetic acid (4 ml), THF (2 ml) and water (1 ml) was heated at 80° C. for 17 h prior to concentration in vacuo. The residue was purified by chromatography (Hexane-EtOAc 2:1, biotage) to give the title compound (33.5 mg).

LCMS RT=3.22 min

(v) 8-Hydroxy-5-((1R)-1-hydroxy-2-{[6-(4-phenyl-butoxy)hexyl]amino}ethyl)quinolin-2(1H)-one acetate A solution of 8-(benzyloxy)-5-((1R)-2-{benzyl[6-(4-phenylbutoxy)hexyl]amino}-1-hydroxyethyl)quinolin-2(1H)-one (33 mg) in ethanol (15 ml) and acetic acid (0.4 ml) was stirred under hydrogen in the presence of palladium on charcoal (10 mg) for 4 h. The reaction mixture was filtered and concentrated in vacuo. The residue was purified by chromatography (SPE, gradient from DCM to DCM-MeOH—NH$_3$ (aq) 100:10:1) to give the title compound (19.5 mg).
LCMS RT=2.66 min ES+ve 452 (MH)$^+$

EXAMPLE 2

3-{4-[(6-{[(2R)-2-Hydroxy-2-(8-hydroxy-2-oxo-1,2-dihydroquinolin-5-yl)ethyl]amino}hexyl)oxy]butyl}benzenesulfonamide acetate

(i) 6-Bromohexyl but-3-ynyl ether

A mixture of 50% w/v aqueous sodium hydroxide (2500 ml), 1,6-dibromohexane (2610 g) and tetra-butylammonium bromide (25 g) was warmed to 50° C., with stirring. But-3-yn-1-ol (500 g) was then added to the reaction mixture at such a rate as to ensure the content's temperature did not exceed 65° C. The reaction was left at 50° C. overnight before being cooled to room temperature. Tert-butyl methyl ether (2500 ml) and brine (2000 ml) was added to the cooled mixture and the layers allowed to separate. The ethereal layer was washed with water (2×2000 ml), brine (1×2000 ml), and then dried over anhydrous MgSO$_4$. The solution was filtered and concentrated under reduced pressure to give crude product as a liquid. This was further purified by fractional distillation using a 60 cm vacuum jacketed Vigreux column at ca. 0.5 mbar. The product was obtained in the fraction which boiled at 92-98° C., to give the title compound (518 g), LC RT=6.16 min.

(ii) 3-{4-[(6-Bromohexyl)oxy]but-1-ynyl}benzenesulfonamide

A mixture of 3-bromo-benzenesulfonamide (625 g), 6-bromohexyl but-3-ynyl ether (850.1 g), bis(triphenylphosphine) palladium (II) chloride (62.5 g), triphenylphosphine (18.1 g) and triethylamine (536.3 g) in tetrahydrofuran (6250 ml) was stirred under an atmosphere of nitrogen for 20 min. Copper (I) iodide (12.5 g) was then added to give a dark red/brown mixture that was heated to 50° C. for 23 h. The reaction mixture was then cooled to room temperature and filtered through a short silica pad (1000 g). The pad was washed with additional tetrahydrofuran (15.6L) and the resulting solution then concentrated under reduced pressure to give crude product (1382 g) as a viscous oil. This was purified by chromatography (7 kg silica) eluting with petroleum ether-ethyl acetate (5:1) followed by petroleum ether-ethyl acetate (2:1) to give the title compound (932.9 g) as an oil, LC RT=5.69 min.

(iii) 3-{4-[(6-Bromohexyl)oxy]butyl}benzenesulfonamide

3-{4-[(6-Bromohexyl)oxy]but-1-ynyl}benzenesulfonamide (627 g) in IMS (1900 ml) was stirred with activated charcoal (314 g) at room temperature for 2 h and then filtered through a short pad of Celite. The filter pad was washed with IMS (4300 ml) and the filtrate transferred to a hydrogenation vessel. 5% Platinum on Charcoal (520.1 g, ~50% water) was added and the reaction mixture was then stirred under an atmosphere of hydrogen (0.2 bar) at 20° C. for 6 h. The mixture was then filtered through a short pad of Celite and concentrated under reduced pressure to give the title compound (499 g) as a solid, LC RT=5.66 min.

(iv) 3-(4-{[6-(Benzylamino)hexyl]oxy}butyl)benzenesulfonamide

3-[4-(6-Bromo-hexyloxy)-butyl]benzenesulfonamide (1.0 g) in toluene (4 ml) was added dropwise to benzylamine (0.65 g) and the resulting mixture heated at 80° C. for 6 h. The mixture was then cooled and 20% aqueous sodium hydroxide solution (50 ml) was added. The resulting mixture was extracted with ethyl acetate and the combined organic layers evaporated to dryness in vacuo. The residual oil was then purified by chromatography (DCM-IMS-NH$_3$(aq) 100:10:1) to give the title compound (0.54 g) LC RT=3.89 min.

(v) 3-(4-{[6-(Benzyl{(2R)-2-[8-(benzyloxy)-2-oxo-1,2-dihydroquinolin-5-yl]-2-acetyl}amino)hexyl]oxy}butyl)benzenesulfonamide A solution of 8-benzyloxy-5-bromoacetylcarbostyril (100 mg) (EP 147719A2) in dry DMF was treated with 3-(4-{[6-(benzylamino)hexyl]oxy}butyl)benzenesulfonamide (172 mg) and diisopropylethylamine (94.5 μl) and stirred at 40° C. for 2 h prior to concentration in vacuo. The residue was purified by chromatography (SPE, gradient from DCM to DCM-MeOH—NH$_3$(aq) 100:10:1) to give the title compound (56 mg).
LCMS RT=2.95 min.

(vi) 3-(4-{[6-(Benzyl{(2R)-2-[8-(benzyloxy)-2-oxo-1,2-dihydroquinolin-5-yl]-2-hydroxyethyl}amino)hexyl]oxy}butyl)benzenesulfonamide A solution of [(R)-tetrahyro-1-methyl-3,3-diphenyl-1H,3H-pyrrolo[1,2-c] [1,3,2]-oxazaborole] (108 μL) in THF (1 ml) was added to borane dimethylsulfide complex in THF (2M, 54 μl) and stirred at 0° C. for 10 min. The reaction mixture was cooled to −10° C. and treated with a solution of 3-(4-{[6-(benzyl{(2R)-2-[8-(benzyloxy)-2-oxo-1,2-dihydroquinolin-5-yl]-2-acetyl}amino)hexyl]oxy}butyl)benzenesulfonamide (64 mg) in THF (3 ml). The reaction mixture was stirred for 16 h at 0° C. prior to quenching with 2N HCl(aq). The reaction mixture was partitioned between 2N HCl(aq) and ethyl acetate. The organic phase was dried and concentrated in vacuo. The residue was purified by chromatography (biotage, DCM-MeOH—NH$_3$(aq) 400:10:1) to give the title compound (10 mg).
LCMS RT=2.91 min.

(vii) 3-{4-[(6-{[(2R)-2-Hydroxy-2-(8-hydroxy-2-oxo-1,2-dihydroquinolin-5-yl)ethyl]amino}hexyl)oxy]butyl}benzenesulfonamide acetate A solution of 3-(4-{[6-(Benzyl{(2R)-2-[8-(benzyloxy)-2-oxo-1,2-dihydroquinolin-5-yl]-2-hydroxyethyl}amino)hexyl]oxy}butyl)benzenesulfonamide (10 mg) in ethanol (10 ml) and acetic acid (0.1 ml) was stirrer under hydrogen in the presence of palladium on charcoal (5 mg) for 2 h. The reaction mixture was filtered and concentrated in vacuo. The residue was purified by chromatography (SPE, gradient from DCM to DCM-MeOH—NH₃(aq) 100:10:1) and freeze-dried from water-acetic acid to give the title compound (5.8 mg).
LCMS RT=2.28 min ES+ve 532 (MH)⁺

EXAMPLE 3

5-Hydroxy-8-(1-hydroxy-2-{[6-(4-phenylbutoxy)hexyl]amino}ethyl)-2H-1,4-benzoxazin-3(4H)-one acetate (i) 5-(Benzyloxy)-8-(2-{benzyl[6-(4-phenylbutoxy)hexyl]amino}-1-hydroxyethyl)-2H-1,4-benzoxazin-3(4H)-one A solution of 5-(benzyloxy)-8-(dihydroxyacetyl)-2H-1,4-benzoxazin-3(4H)-one (DE 3134590 A1) (150 mg) in dry DCM (2 ml) was treated with acetic acid and N-benzyl-6-(4-phenylbutoxy)hexan-1-amine (320 mg) (*Tetrahedron Letters*. 1994, 35, 9375) and stirred for 4 hr. Sodium triacetoxyborohydride (216 mg) was added and the reaction mixture stirred at room temperature for 3 days. Sodium borohydride (35 mg) in methanol (2 ml) was added and stirring continued for a further 2 h. The reaction mixture was quenched with water and partitioned between water and DCM. The organic phase was dried and concentrated in vacuo. The residue was purified by chromatography (Hexane-EtOAc, SPE) to give the title compound as a mixture with 5-(benzyloxy)-8-({benzyl[6-(4-phenylbutoxy)hexyl]amino}acetyl)-2H-1,4-benzoxazin-3(4H)-one (81.6 mg).
LCMS RT=3.24 min.

(ii) 5-Hydroxy-8-(1-hydroxy-2-{[6-(4-phenylbutoxy)hexyl]amino}ethyl)-2H-1,4-benzoxazin-3(4H)-one acetate A solution of 5-(benzyloxy)-8-(2-{benzyl[6-(4-phenylbutoxy)hexyl]amino}-1-hydroxyethyl)-2H-1,4-benzoxazin-3(4H)-one (82 mg) in ethanol (10 ml) and ethyl acetate (2 ml) was stirrer under hydrogen in the presence of palladium on charcoal (50 mg) for 8 h. The reaction mixture was filtered and concentrated in vacuo. Mass directed auto-preparative chromatography afforded the title compound (13.7 mg).
LCMS RT=2.62 min ES+ve 456 (MH)⁺

EXAMPLE 4

3-{4-[(6-{[2-Hydroxy-2-(5-hydroxy-3-oxo-3,4-dihydro-2H-1,4-benzoxazin-8-yl)ethyl]amino}hexyl)oxy]butyl}benzenesulfonamide (i) 3-(4-{[6-(Benzyl{2-[5-(benzyloxy)-3-oxo-3,4-dihydro-2H-1,4-benzoxazin-8-yl]-2-hydroxyethyl}amino)hexyl]oxy}butyl)benzenesulfonamide Prepared by methods similar to that described for Example 3i as a mixture with 3-(4-{[6-(benzyl{2-[5-(benzyloxy)-3-oxo-3,4-dihydro-2H-1,4-benzoxazin-8-yl]-2-acetyl}amino)hexyl]oxy}butyl)benzenesulfonamide (22.3 mg).
LCMS RT=2.83 min (ii) 3-{4-[(6-{[2-Hydroxy-2-(5-hydroxy-3-oxo-3,4-dihydro-2H-1,4-benzoxazin-8-yl)ethyl]amino}hexyl)oxy]butyl}benzenesulfonamide Prepared by methods similar to that described for Example 3ii LCMS RT=2.32 min
ES+ve 536 (MH)⁺

EXAMPLE 5

4-Hydroxy-7-((1R)-1-hydroxy-2-{[6-(4-phenylbutoxy)hexyl]amino}ethyl)-1,3-benzothiazol-2(3H)-one formate (i) 7-Acetyl-4-methoxy-1,3-benzothiazol-2(3H)-one A solution of 4-methoxy-1,3-benzothiazol-2(3H)-one (DE 3017977 A1) (1.92 g) in dry dichloromethane (50 ml) was cooled to −5° C. under nitrogen. Acetyl chloride (1.43 ml) and aluminium chloride (3.43 g) were added in one portion, and stirred for 2 h at RT. The reaction was quenched carefully with water, followed by addition of 2N HCl and dichloromethane. The aqueous layer was extracted with dichloromethane, and the combined organic layers were washed with brine and dried (Na₂SO₄) and evaporated in vacuo to give the title compound (1.92 g). LCMS RT=2.50 min (ii) 7-Acetyl-4-hydroxy-1,3-benzothiazol-2(3H)-one A mixture of 7-acetyl4-methoxy-1,3-benzothiazol-2(3H)-one (1.2 g), pyridine hydrochloride (2.77 g), in dry 1-methyl-2-pyrrolidone(6 ml), was heated at 190° C. in a microwave reactor for 90 min. The reaction mixture was cooled to room temperature, and diluted with water. The precipitated solid was collected by filtration, washed with water and dried under vacuum at 40° C. to give the title compound (1.07 g). LCMS RT=2.46 min.

(iii) 7-Acetyl-4-(benzyloxy)-1,3-benzothiazol-2(3H)-one

To a solution of 7-acetyl-4-hydroxy-1,3-benzothiazol-2(3H)-one (153 mg), in dry THF (3 ml) and dry DMF (0.5 ml) under nitrogen, was added N,N-diisopropylethylamine (0.13 ml) and benzyl bromide (0.09 ml), and the mixture stirred for 72 h. Water (10 ml) was added and the mixture extracted with ethyl acetate. The organic phases were combined, washed with brine, dried (MgSO₄), and evaporated in vacuo. The residue was purified on a 5 g silica SPE cartridge, eluting with a stepped gradient of 10% to 50% ethyl acetate-cyclohexane mixtures, to give the title compound (68 mg). LCMS RT=3.14 min.

(iv) 4-(Benzyloxy)-7-(bromoacetyl)-1,3-benzothiazol-2(3H)-one

To a solution of 7-acetyl-4-(benzyloxy)-1,3-benzothiazol-2(3H)-one (68 mg) in dry THF (3 ml) under nitrogen, was added phenyltrimethylammonium tribromide (90 mg) and the mixture heated at 80° C. under nitrogen for 2 h. The mixture was diluted with water, extracted with ethyl acetate, dried (MgSO₄), filtered and evaporated in vacuo. The residue was purified on a 5 g silica SPE cartridge, eluting with stepped gradient of 10% to 100% ethyl acetate-cyclohexane mixtures, to give the title compound (49 mg).
LCMS RT=3.13 min.

(v) 4-(Benzyloxy)-7-[(1R)-2-bromo-1-hydroxyethyl]-1,3-benzothiazol-2(3H)-one

A solution of [(R)-tetrahyro-1-methyl-3,3-diphenyl-1H,3H-pyrrolo[1,2-c] [1,3,2]-oxazaborole] (22 µl of 1M in toluene) in dry THF(1 ml) was cooled to −5° C., stirring under nitrogen. Borane-methyl sulfide complex (2M solution in THF, 11 µl) was added and stirred for 10 min at −5° C. A solution of 4-(benzyloxy)-7-(bromoacetyl)-1,3-benzothiazol-2(3H)-one (47 mg) in dry THF (1.5 ml) was added dropwise and then another 66 μl of borane-methyl sulfide complex (2M solution in THF). The reaction mixture was left for 72 h at less than 5° C. and then partitioned between 2N HCl and ethyl acetate. The organic solution was dried (MgSO₄), filtered and evaporated in vacuo. The residue was purified on a 5 g silica SPE cartridge, eluting with a stepped gradient of 10% to 25% ethyl acetate-cyclohexane mixtures to give the title compound (33 mg). LCMC RT=3.19 min.

(vi) 4-(Benzyloxy)-7-{(1R)-2-bromo-1-[tetrahydro-2H-pyran-2-yloxy]ethyl}-1,3-benzothiazol-2(3H)-one To a stirred solution of 4-(benzyloxy)-7-[(1R)-2-bromo-1-hydroxyethyl]-1,3-benzothiazol-2(3H)-one (31 mg) in dry DCM (5 ml) under nitrogen, was added pyridinium p-toluenesulphonate (5 mg), followed by 3,4-dihydro-2H-pyran (30 μl). The mixture was evaporated in vacuo after 18 h and purified on a 2 g silica SPE cartridge, eluting with a stepped gradient 10% to 100% DCM-cyclohexane mixtures, to give the title compound (42 mg). LCMS RT=3.72 and 3.78 min.

(vii) 4-(Benzyloxy)-7-{(1R)-2-{benzyl[6-(4-phenylbutoxy)hexyl]amino}-[tetrahydro-2H-pyran-2-yloxy]ethyl}-1,3-benzothiazol-2(3H)-one A mixture of 4-(benzyloxy)-7-{(1R)-2-bromo-1-[tetrahydro-2H-pyran-2-yloxy]ethyl}-1,3-benzothiazol-2(3H)-one (42 mg), N,N-diisopropylethylamine (32 μl), and N-benzyl-6-(4-phenylbutoxy)hexan-1-amine (*Tetrahedron Letters*. 1994, 35, 9375) (47.5 mg), was heated at 120° C. in a reactivial for 18 h. The mixture was dissolved in DCM and purified on a 12 g biotage cartridge, eluting with 15% ethyl acetate-cyclohexane mixture to give the title compound (10 mg). LCMS RT=3.62 and 3.66 min.

(viii) 4-(Benzyloxy)-7-((1R)-2-{benzyl[6-(4-phenylbutoxy)hexyl]amino}-hydroxyethyl)-1,3-benzothiazol-2(3H)-one To a solution of 4-(benzyloxy)-7-{(1R)-2-{benzyl[6-(4-phenylbutoxy)hexyl]amino}-1-[tetrahydro-2H-pyran-2-yloxy]ethyl}-1,3-benzothiazol-2(3H)-one (10 mg) in dry DCM (1 ml) and methanol (0.1 ml) stirring under nitrogen, was added p-toluenesulphonic acid (10 mg). After 18 h 2N sodium bicarbonate was added and the mixture extracted with DCM. The organic solution was diluted with cyclohexane and the mixture purified on a 5 g silica SPE cartridge to give the title compound (7.4 mg). LCMS RT=3.13 min.

(ix) 4-Hydroxy-7-((1R)-1-hydroxy-2-{[6-(4-phenylbutoxy)hexyl]amino}ethyl)-1,3-benzothiazol-2(3H)-one formate 4-(Benzyloxy)-7-((1R)-2-{benzyl[6-(4-phenylbutoxy)hexyl]amino}-1-hydroxyethyl)-1,3-benzothiazol-2(3H)-one (7.4 mg) was dissolved in 98% formic acid (0.5 ml)and palladium black catalyst (4 mg) added. After stirring for 8 h, the catalyst was removed by filtration through celite and the filtrate evaporated in vacuo. The residue was purified on mass directed autoprep, to give the title compound (0.51 mg). LCMS RT=2.95 min. ES+ve 459 (M+H)⁺

EXAMPLE 6

4-Hydroxy-7-(1-hydroxy-2-{[6-(4-phenylbutoxy)hexyl]amino}ethyl)-1,3-benzothiazol-2(3H)-one formate (i) 7-Acetyl-2-oxo-2,3-dihydro-1,3-benzothiazol-4-yl benzyl carbonate A mixture of 7-acetyl-4-hydroxy-1,3-benzothiazol-2(3H)-one (209 mg) in dry THF (5 ml) and DCM (5 ml) with pyridine (0.2 ml), stirring under nitrogen, was cooled to −10° C. and benzylchloroformate (0.37 mls) was added. After 18 h stirring at room temperature, the mixture was diluted with water and extracted into DCM. The solution was dried (MgSO₄), filtered, and evaporated in vacuo. The residue was purified on a 10 g silica SPE cartridge, eluting with a stepped gradient of 25% to 100% ethyl acetate-cyclohexane mixtures, to give the title compound (280 mg). LCMS RT=3.19 min.

(ii) Benzyl 7-(bromoacetyl)-2-oxo-2,3-dihydro-1,3-benzothiazol-4-yl carbonate

To a solution of 7-acetyl-2-oxo-2,3-dihydro-1,3-benzothiazol-4-yl benzyl carbonate (280 mg) in dry THF (20 ml) stirring under nitrogen, was added phenyltrimethylammonium tribromide (330 mg). The mixture was heated at 80° C. for 2 h and then diluted with water, extracted with ethyl acetate, dried (MgSO₄), filtered, and evaporated in vacuo. The residue was purified on a 40 g silica biotage cartridge and eluted with 20% ethyl acetate-cyclohexane to give the title compound (186 mg). LCMS RT=3.43 min.

(iii) 7-({Benzyl[6-(4-phenylbutoxy)hexyl]amino}acetyl)-4-hydroxy-1,3-benzothiazol-2(3H)-one To a solution of benzyl 7-(bromoacetyl)-2-oxo-2,3-dihydro-1,3-benzothiazol-4-yl carbonate (50 mg) in dry DMF (1 ml) stirring under nitrogen was added N-benzyl-6-(4-phenylbutoxy)hexan-1-amine (*Tetrahedron Letters*. 1994, 35, 9375) (60 mg) and N,N-diisopropylethylamine (32 μl). After stirring at 40° C. for 2 h, 2N HCl was added and the mixture extracted with ethyl acetate. The solution was dried (MgSO₄), filtered and evaporated in vacuo. The residue was purified on a 5 g silica SPE cartridge, eluting with a stepped gradient of 2% to 10% methanol-dichloromethane mixtures to give the title compound (50 mg). LCMS RT=3.14 min.

(iv) 4-Hydroxy-7-({[6-(4-phenylbutoxy)hexyl]amino}acetyl)-1,3-benzothiazol-2(3H)-one A solution of 7-({benzyl[6-(4-phenylbutoxy)hexyl]amino}acetyl)-4-hydroxy-1,3-benzothiazol-2(3H)-one (100 mg) in dry ethanol (10 ml) and acetic acid (0.5 ml) was added to 10% Pd/C catalyst (40 mg) and stirred under hydrogen for 20 h. The catalyst was collected by filtration through celite and the filtrate evaporated in vacuo. The residue was purified on SCX and then silica SPE cartridge, eluting with a stepped gradient of 1-10% methanol-dichloromethane mixtures, to give the title compound (9 mg). LCMS RT=2.81 min.

(v) 4-Hydroxy-7-(1-hydroxy-2-{[6-(4-phenylbutoxy)hexyl]amino}ethyl)-1,3-benzothiazol-2(3H)-one formate Sodium borohydride (4 mg) was added to a solution of 4-hydroxy-7-({[6-(4-phenylbutoxy)hexyl]amino}acetyl)-1,3-benzothiazol-2(3H) one (9 mg) in dry ethanol (2 ml). The mixture was stirred under nitrogen for 2 h, and then quenched with water and evaporated in vacuo. The residue was purified by mass directed autoprep. to give the title compound (1.5 mg). LCMS RT=2.74 min, ES+ve 459 (M+H)$^+$

EXAMPLE 7

3-{4-[(6-{[(2R)-2-(3-Fluoro-4-hydroxyphenyl)-2-hydroxyethyl]amino}hexyl)oxy]butyl}benzenesulfonamide formate i) 2-Azido-1-[4-(benzyloxy)-3-fluorophenyl]ethanone A solution of 2-bromo-1-[4-(benzyloxy)-3-fluorophenyl]ethanone (*J. Med. Chem.* 1980, 23, 738-744) (1 g) in dry DMF (2.5 mL) was cooled to 15° C. and treated portionwise with sodium azide (220 mg). After complete addition the reaction mixture was stirred for a further 1 h. The reaction mixture was partitioned between EtOAc and water. The organic phase was washed with water and the combined aqueous phase back extracted with EtOAc. The combined organic phase was washed with sat. NaHCO$_{3(aq)}$ three times and the combined washes back extracted with EtOAc. The combined organic phase was washed with brine, dried and concentrated in vacuo. The residue was purified by column chromatography on silica, eluting with hexane-EtOAc (4:1 and 2:1) to give the title compound (810 mg). LCMS RT=3.61 min.

ii) (1R)-2-Azido-1-[4-(benzyloxy)-3-fluorophenyl]ethanol

Borane-dimethylsulphide solution in THF (2M, 0.03 mL) was added to a solution of (R)-2-methyl-CBS-oxazaborolidine in toluene (1M, 0.06 mL) at 0° C. with stirring. The reaction mixture was stirred for 15 min prior to the dropwise addition of a solution of 2-azido-1-[4-(benzyloxy)-3-fluorophenyl]ethanone (100 mg) in THF. Further Borane-dimethylsulphide in THF (2M, 0.03 mL) was added dropwise and the reaction mixture stirred at 0° C. for 2 h. 2M HCl$_{(aq)}$ (2 mL) was added dropwise and the reaction mixture stirred for 10 min prior to partitioning the reaction mixture between ether and water. The organic phase was washed twice with 2M HCl$_{(aq)}$, three times with sat. NaHCO$_{3(aq)}$, water and brine. The organic phase was dried and concentrated in vacuo. The residue was purified by column chromatography on silica gel, eluting with DCM to give the title compound (470 mg). LCMS RT=3.36 min.

iii) (1R)-2-Amino-1-[4-(benzyloxy)-3-fluorophenyl]ethanol

A solution of (1R)-2-azido-1-[4-(benzyloxy)-3-fluorophenyl]ethanol (410 mg) in THF (8 mL) and water (2 mL) was treated with PPh$_3$ (410 mg) and stirred for 1 h prior to addition of further with PPh$_3$ (220 mg). After stirring for a further 4 h the reaction mixture was concentrated in vacuo and the residue partitioned between EtOAc and water. The organic phase was washed three times with 5% NaHCO$_{3(aq)}$ dried and concentrated in vacuo. The residue was purified by chromatography on silica gel, eluting with DCM, 1% MeOH in DCM, 2% MeOH in DCM, 5% MeOH containing 0.5% Et$_3$N in DCM, and finally 20% MeOH containing 1% Et$_3$N in DCM) to give the title compound (260 mg). LCMS RT=2.16 min.

iv) 4-[(1R)-2-Amino-1-hydroxyethyl]-2-fluororhenol

Palladium on carbon (10% Pd by weight, wet, 50 mg) was flushed with nitrogen and treated with a solution of (1R)-2-amino-1-[4-(benzyloxy)-3-fluorophenyl]ethanol (500 mg) in ethanol (25 mL), EtOAc (25 mL) and acetic acid (10 mL). The reaction mixture was stirred under hydrogen for 5 h prior to flushing the reaction mixture with nitrogen and filtering to remove the catalyst and concentrating in vacuo. The residue was purified by chromatography (SCX, eluted with DCM, MeOH and DCM-MeOH—NH$_3$(aq) 100:10:1) to give the title compound (308 mg). $\delta_H$ (400 MHz, CD$_3$OD) 7.05 (1H, dd, J 2, 12 Hz), 6.94 (1H, dd, J 2, 9 Hz), 6.86 (1H, t, J 9 Hz), 4.54 (1H, dd, J 5, 8 Hz), 2.78 (1H, d, J 5 Hz), 2.77 (1H, d, J 8 Hz).

v) 3-{4-[(6-{[(2R)-2-(3-Fluoro-4-hydroxyphenyl)-2-hydroxyethyl]amino}hexyl)oxy]butyl}benzenesulfonamide formate A stirred solution of 4-[(1R)-2-amino-1-hydroxyethyl]-2-fluorophenol (45 mg), diisopropylethylamine (0.06 ml) and 3-{4-[(6-bromohexyl)oxy]butyl}benzenesulfonamide (86 mg) in N,N-dimethylformamide (1 ml) under nitrogen was heated to 50° for 18 h. The mixture was cooled to 20°, the solvent evaporated in vacuo and the residue purified by mass-directed autopreparative HPLC to give the title compound (36 mg). LCMS RT=2.37 min, ES+ve 483 (MH)$^+$.

EXAMPLE 8

3-(4-{[6-({2-Hydroxy-2-[5-hydroxy-6-(hydroxymethyl)pyridin-2-yl]ethyl}amino)hexyl]oxy}butyl)benzenesulfonamide formate A stirred solution of 2-amino-1-(2-phenyl-4H-[1,3]dioxino[5,4-b]pyridin-6-yl)ethanol (100 mg) (EP220054A2), diisopropylethylamine (0.08 ml) and 3-{4-[(6-bromohexyl)oxy]butyl}benzenesulfonamide (120 mg) in N,N-dimethylformamide (2 ml) under nitrogen was heated to 50° for 18 h. The mixture was cooled to 20° and the solvent evaporated in vacuo. The residue was dissolved in acetic acid (4 ml) and water (2 ml) and was heated to 70° for 18 h. The mixture was cooled to 20°, the solvent evaporated in vacuo and the residue purified by mass-directed autopreparative HPLC to give the title compound (22 mg). LCMS RT=2.23 min, ES+ve 496 (MH)$^+$.

EXAMPLE 9

3-[4-({6-[((2R)-2-Hydroxy-2-{4-hydroxy-3-[(methylsulfonyl)amino]phenyl}ethyl)amino]hexyl}oxy)butyl]benzenesulfonamide formate i) N-[2-Hydroxy-5-((1R)-1-hydroxy-2-{[(1S)-2-hydroxy-1-phenylethyl]amino}ethyl)phenyl]methanesulfonamide A solution of N-[5-(bromoacetyl)-2-hydroxyphenyl]methanesulfonamide (*J. Med. Chem.* 1967, 10, 462-72) (1.15 g) in dry DMF (30 mL) was treated with diisopropylethylamine (1.06 mL) and (S)-phenylglycinol (474 mg) and the reaction mixture stirred at room temperature for 4 h. The reaction mixture was concentrated in vacuo and the residue re-suspended in methanol (50 mL). The reaction mixture was cooled to 0° C. and treated with CaCl$_2$ (1.27 g). The reaction mixture was stirred at 0° C. for 30 min prior to portionwise addition of NaBH$_4$ (218 mg) ensuring that the temperature did not rise above 10° C. After complete addition the reaction mixture was allowed to warm to room temperature and stirred for a further 74 h. The reaction mixture was concentrated in vacuo and the residue partitioned between EtOAc and water. The organic phase was dried and concentrated in vacuo. The mixture was purified by chromatography (SPE, gradient from DCM to DCM-MeOH—NH$_3$(aq) 100:10:1) afforded the title compound (85 mg). LCMS RT=2.48 min ii) N-{5-[(1R)-2-Amino-1-hydroxyethyl]-2-hydroxyphenyl}methanesulfonamide Palladium hydroxide (40 mg, 50% water) was flushed with nitrogen and treated with a solution of N-[2-hydroxy-5-((1R)-1-hydroxy-2-{[(1S)-2-hydroxy-1-phenylethyl]amino}ethyl)phenyl]methanesulfonamide (400 mg) in methanol (80 mL) and acetic acid (0.5 mL). The reaction mixture was stirred under hydrogen for 16 h prior to flushing the reaction mixture with nitrogen and filtering to remove the catalyst and concentrating in vacuo. The residue was purified by chromatography (OASIS, eluted with water, 5% MeOH in water 50% MeOH in water and MeOH) to give the title compound (182 mg). $\delta_H$ (400 MHz, CD$_3$OD) 7.38 (1H, d, J 2 Hz), 7.12 (1H, dd, J 2, 8 Hz), 6.90 (1H, d, J 8 Hz), 4.78 (1H, dd, J 2, 10 Hz), 3.08 (1H, dd, J 2, 15 Hz), 2.98 (1H, bd, J 10 Hz), 2.93 (3H, s).

iii) 3-[4-({6-[((2R)-2-Hydroxy-2-{4-hydroxy-3-[(methylsulfonyl)amino]phenyl}ethyl)amino]hexyl}oxy)butyl]benzenesulfonamide formate A stirred solution of 1-{5-[(1R)-2-amino-1-hydroxyethyl]-2-hydroxyphenyl}methanesulfonamide (65 mg), diisopropylethylamine (0.06 ml) and 3-{4-[(6-bromohexyl)oxy]butyl}benzenesulfonamide (86 mg) in N,N-dimethylformamide (1 ml) under nitrogen was heated to 50° for 48 h. The mixture was cooled to 20°, the solvent evaporated in vacuo and the residue purified by mass-directed autopreparative HPLC to give the title compound (12 mg). LCMS RT=2.31 min ES+ve 558 (MH)$^+$.

EXAMPLE 10

3-{3-[(7-{[(2R)-2-(3-Fluoro-4-hydroxyphenyl)-2-hydroxyethyl]amino}heptyl)oxy]propyl}benzenesulfonamide formate Prepared using methods similar to those described in Example 7.
LCMS RT=2.37 min, ES+ve 483 (MH)$^+$.

EXAMPLE 11

3-(3-{[7-({2-Hydroxy-2-[5-hydroxy-6-(hydroxymethyl)pyridin-2-yl]ethyl}amino)heptyl]oxy}propyl)benzenesulfonamide formate Prepared using methods similar to those described in Example 8.
LCMS RT=2.22 min, ES+ve 496 (MH)$^+$.

EXAMPLE 12

3-[3-({7-[((2R)-2-Hydroxy-2-{4-hydroxy-3-[(methylsulfonyl)amino]phenyl}ethyl)amino]heptyl}oxy)propyl]benzenesulfonamide formate Prepared using methods similar to those described in Example 9.
LCMS RT=2.33 min, ES+ve 558 (MH)$^+$.

EXAMPLE 13

3-{3-[(7-{[(2R)-2-Hydroxy-2-(8-hydroxy-2-oxo-1,2-dihydroquinolin-5-yl)ethyl]amino}heptyl)oxy]propyl}benzenesulfonamide acetate i) 5-[(1R)-2-(Benzylamino)-1-hydroxyethyl]-8-(benzyloxy)quinolin-2(1H)-one 8-(Benzyloxy)-5-[(2R)-oxiran-2-yl]quinolin-2(1H)-one (0.102 g) (WO 9525104), was dissolved in benzylamine (0.5 ml) and heated in a microwave oven for 15 min at 150° C. Excess benzylamine was removed by evaporation on a rotary evaporator and the residue was purified on a silica SPE cartridge using methanol-dichloromethane-0.880 ammonia mixtures, to give the title compound (106 mg) LCMS RT=2.30 min ii) 3-(3-{[7-(Benzyl{(2R)-2-[8-(benzyloxy)-2-oxo-1,2-dihydroquinolin-5-yl]-2-hydroxyethyl}amino)heptyl]oxy}propyl)benzenesulfonamide 5-[(1R)-2-(Benzylamino)-1-hydroxyethyl]-8-(benzyloxy)quinolin-2(1H)-one (48 mg) was dissolved in acetonitrile (2 ml). N,N-diisopropylethylamine (0.042 ml), and 3-{3-[(7-bromoheptyl)oxy]propyl}benzenesulfonamide (43 mg) were added to the solution, which was heated at reflux for 72 h under nitrogen. The mixture was diluted with water and extracted with ethyl acetate. The organic extracts were combined, dried (MgSO$_4$) and evaporated in vacuo. The residue was purified on a silica SPE cartridge eluting with ethyl acetate-cyclohexane mixtures to give the title compound (36 mg). LCMS RT=2.76 min iii) 3-{3-[(7-{[(2R)-2-Hydroxy-2-(8-hydroxy-2-oxo-1,2-dihydroquinolin-5-yl)ethyl]amino}heptyl)oxy]propyl}benzenesulfonamide acetate A solution of 3-(3-{[7-(benzyl{(2R)-2-[8-(benzyloxy)-2-oxo-1,2-dihydroquinolin-5-yl]-2-hydroxyethyl}amino)heptyl]oxy}propyl)benzenesulfonamide (36 mg) in ethanol (10 ml) with ethyl acetate (2 ml) and glacial acetic acid (1 ml) was hydrogenated using 10% palladium on carbon (50% water by weight, 10 mg) and 20% palladium hydroxide on carbon (10 mg) for 19 h. The catalyst was removed by filtration and the filtrate was evaporated in vacuo. The residue was purified on an aminopropyl SPE cartridge (2 g), eluting with methanol-dichloromethane mixtures. Evaporation of the appropriate fractions with glacial acetic acid gave the title compound (15 mg). LCMS RT=2.26 min ES+ve m/z 532 (MH)$^+$ Biological Activity The potencies of the aforementioned compounds were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of examples 1-13 had $IC_{50}$ values below 1 µM.

Potency at other beta adrenoreceptor subtypes was determined using chinese hamster ovary cells transfected with either the human beta 1 adrenoreceptor or the human beta 3 adrenoreceptor. Agonist activity was assessed by measuring changes in intracellular cyclic AMP.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I)

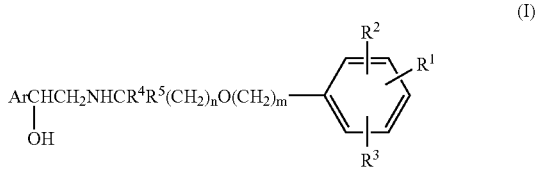

(I)

or a salt thereof, wherein:

n is an integer of from 2 to 8;

m is an integer of from 3 to 11, with the proviso that the sum of n+m is from 5 to 19;

$R^1$ is —$XSO_2NR^6R^7$;

wherein X is —$(CH_2)_p$- or $C_{2-6}$ alkenylene;

p is an integer from 0 to 6;

$R^6$ and $R^7$ are independently selected from hydrogen, $C_{1-6}$alkyl, $C_{3-7}$cycloalkyl, $CONR^8R^9$, phenyl and phenyl($C_{1-4}$alkyl)-, or $R^6$ and $R^7$, together with the nitrogen atom to which they are bonded, form a 5-, 6- or 7- membered nitrogen containing ring;

and $R^6$ and $R^7$ are each independently optionally substituted by 1 or 2 groups independently selected from halo, $C_{1-6}$alkyl, $C_{1-6}$alkoxy, hydroxy-substituted $C_{1-6}$alkoxy, $C_{1-6}$haloalkyl, $CO_2R^8$, $SO_2R^8R^9$, —$CONR^8R^9$, —$NR^8C(O)R^9$ or a 5-, 6- or 7-membered heterocyclic ring;

$R^8$ and $R^9$ are independently selected from hydrogen, $C_{1-6}$alkyl, $C_{3-7}$cycloalkyl, phenyl and phenyl($C_{1-6}$alkyl)-;

$R^2$ and $R^3$ are independently selected from hydrogen, $C_{1-6}$alkyl, $C_{1-6}$alkoxy, halo, phenyl and $C_{1-6}$haloalkyl;

$R^4$ and $R^5$ are independently selected from hydrogen and $C_{1-4}$ alkyl with the proviso that the total number of carbon atoms in $R^4$ and $R^5$ is not more than 4, and Ar is a group selected from the group consisting of:

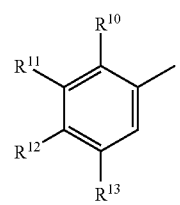

(a)

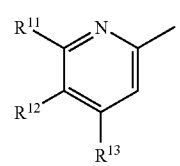

(b)

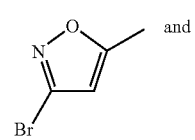

(c)

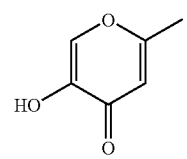

(d)

wherein $R^{11}$ represents hydrogen, halogen, —$(CH_2)_qOR^{14}$, —$NR^{14}C(O)R^{15}$, —$NR^{14}SO_2R^{15}$, —$SO_2NR^{14}R^{15}$, —$NR^{14}R^{15}$, —$OC(O)R^{16}$ or $OC(O)NR^{14}R^{15}$, and $R^{10}$ represents hydrogen, halogen or $C_{1-4}$ alkyl;

or $R^{11}$ represents —$NHR^{17}$ and $R^{10}$ and —$NHR^{17}$ together form a 5- or 6-membered heterocyclic ring;

$R^{12}$ represents hydrogen, halogen, —$OR^{14}$ or —$NR^{14}R^{15}$; —$OC(O)R^{16}$ or —$OC(O)NR^{14}R^{15}$;

$R^{13}$ represents hydrogen, halogen, halo$C_{1-4}$ alkyl, —$OR^{14}$ or —$NR^{14}R^{15}$;

$R^{14}$ and $R^{15}$ each independently represents hydrogen or $C_{1-4}$ alkyl, or in the groups —$NR^{14}R^{15}$, —$SO_2NR^{14}R^{15}$ and —$OC(O)NR^{14}R^{15}$, $R^{14}$ and $R^{15}$ independently represent hydrogen or $C_{1-4}$ alkyl or together with the nitrogen atom to which they are attached form a 5-, 6- or 7-membered nitrogen-containing ring, $R^{16}$ represents an aryl group which may be unsubstituted or substituted by one or more substituents selected from halogen, $C_{1-4}$ alkyl, hydroxy, $C_{1-4}$ alkoxy or halo $C_{1-4}$ alkyl; and q is zero or an integer from 1 to 4;

provided that Ar is not a group (a) wherein $R^{11}$ is $(CH_2)_qOR^{14}$ or $NR^{14}COR^{15}$, and $R^{12}$ is $OR^{14}$.

2. A compound of formula (I) according to claim 1 wherein, in the group Ar, $R^{11}$ represents halogen, —$(CH_2)_qOR^{14}$, —$NR^{14}C(O)R^{15}$, —$NR^{14}SO_2R^{15}$, —$SO_2NR^{14}R^{15}$, —$NR^{14}R^{15}$, —$OCO(O)R^{16}$ or $OC(O)NR^{14}R^{15}$, and $R^{10}$ represents hydrogen, or $R^{11}$ represents —$NHR^{17}$ and $R^{10}$ and —$NHR^{17}$ together form a 5- or 6-membered heterocyclic ring; and $R^{13}$ represents hydrogen, halogen, halo, $C_{1-4}$ alkyl, —$OR^{14}$, —$NR^{14}R^{15}$.

3. A compound of formula (I) according to claim 1 wherein the group $R^1$ is attached to the meta-position relative to the —O—$(CH_2)_m$link.

4. A compound of formula (I) according to claim 1 wherein $R^1$ represents $SO_2NR^6R^7$ wherein $R^6$ and $R^7$ are independently selected from hydrogen and $C_{1-6}$alkyl.

5. A compound of formula (I) according to claim 1 wherein $R^4$ and $R^5$ are independently selected from hydrogen and methyl.

6. A compound of formula (I) according to claim 1 wherein $R^2$ and $R^3$ each represent hydrogen.

7. A compound of formula (I) according to claim 1 wherein n is 5 or 6 and m is 3 or 4 such that m+n is 8, 9 or 10.

8. A compound of formula (I) according to claim 1 wherein Ar represents a group selected from the group consisting of:

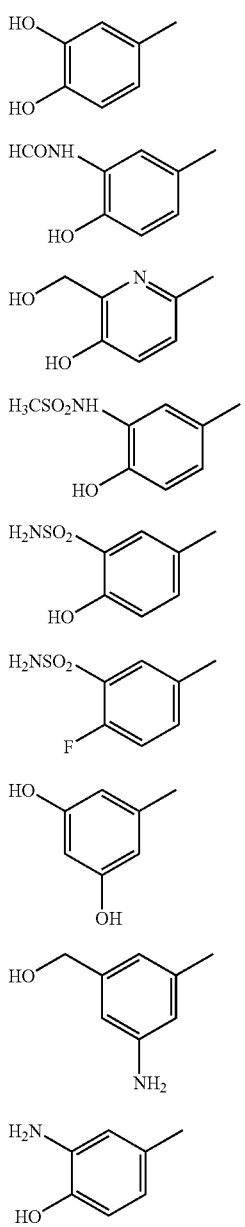

-continued

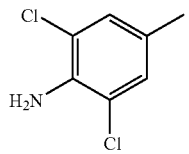
(x)

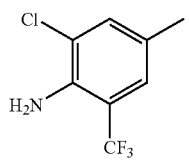
(xi)

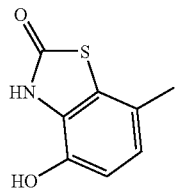
(xiv)

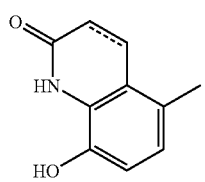
(xv)

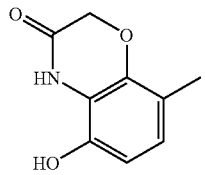
(xvi)

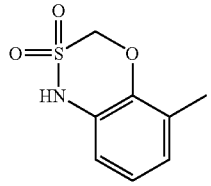
(xvii)

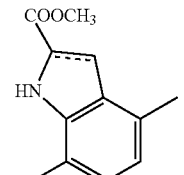
(xviii)

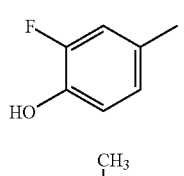
(xix)

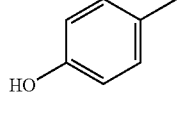
(xx)

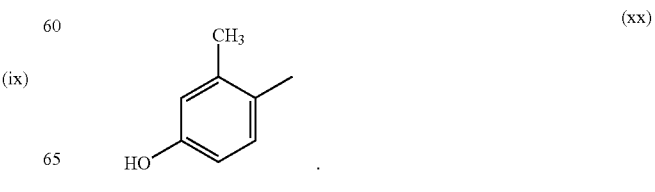

9. A compound of formula (I) according to claim 8 wherein $R^1$ is $XSO_2NR^6R^7$ and Ar is selected from the group consisting of (iii), (iv), (xiv), (xv), (xvi) and (xix).

10. A compound selected from the group consisting of:
8-Hydroxy-5-((1R)-1-hydroxy-2-{[6-(4-phenylbutoxy)hexyl]amino}ethyl)quinolin-2(1H)-one;
3-{4-[(6-{[(2R)-2-Hydroxy-2-(8-hydroxy-2-oxo-1,2-dihydroquinolin-5-yl)ethyl]amino}hexyl)oxy]butyl}benzenesulfonamide;
5-Hydroxy-8-(1-hydroxy-2-{[6-(4-phenylbutoxy)hexyl]amino}ethyl)-2H-1,4-benzoxazin-3(4H)-one;
3-{4-[(6-{[2-hydroxy-2-(5-hydroxy-3-oxo-3,4-dihydro-2H-1,4-benzoxazin-8-yl)ethyl]amino}hexyl)oxy]butyl}benzenesulfonamide;
4-Hydroxy-7-((1R)-1-hydroxy-2-{[6-(4-phenylbutoxy)hexyl]amino}ethyl)-1,3-benzothiazol-2(3H)-one;
4-Hydroxy-7-(1-hydroxy-2-{[6-(4-phenylbutoxy)hexyl]amino}ethyl)-1,3-benzothiazol-2(3H)-one;
3-{4-[(6-{[(2R)-2-(3-Fluoro-4-hydroxyphenyl)-2-hydroxyethyl]amino}hexyl)oxy]butyl}benzenesulfonamide;
3-(4-{[6-({2-Hydroxy-2-[5-hydroxy-6-(hydroxymethyl)pyridin-2-yl]ethyl}amino)hexyl]oxy}butyl)benzenesulfonamide;
3-[4-({6-[((2R)-2-Hydroxy-2-{4-hydroxy-3-[(methylsulfonyl)amino]phenyl}ethyl)amino]hexyl}oxy)butyl]benzenesulfonamide;
3-{3-[(7-{[(2R)-2-(3-Fluoro-4-hydroxyphenyl )-2-hydroxyethyl]amino}heptyl)oxy]propyl}benzenesulfonamide;
3-(3-{[7-({2-Hydroxy-2-[5-hydroxy-6-(hydroxymethyl)pyridin-2-yl]ethyl}amino)heptyl]oxy}propyl)benzenesulfonamide;
3-[3-({7-[((2R)-2-Hydroxy-2-{4-hydroxy-3-[(methylsulfonyl)amino]phenyl}ethyl)amino]heptyl}oxy)propyl]benzenesulfonamide;
3-{3-[(7-{[(2R)-2-Hydroxy-2-(8-hydroxy-2-oxo-1,2-dihydroquinolin-5-yl)ethyl]amino}heptyl)oxy]propyl}benzenesulfonamide;
3-(3-{[7-({(2R)-2-[3-(Formylamino)-4-hydroxyphenyl]-2-hydroxyethyl}amino)heptyl]oxy}propyl)benzenesulfonamide;
and a salt thereof.

11. A process for the preparation of a compound of formula (I), according to claim 1, or a salt thereof, which comprises:
deprotecting a protected intermediate of formula (II):

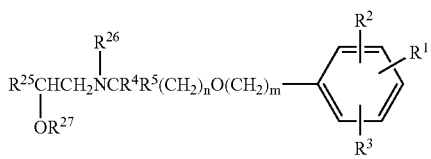

(II)

or a salt thereof, wherein $R^1$, $R^2$, $R^3$, $R^4$, $R^5$, m and n are as defined for the compounds of formula (I) $R^{25}$ represents an optionally protected form of Ar, and $R^{26}$ and $R^{27}$ each independently represent either hydrogen or a protecting group, provided that the compound of formula (II) contains at least one protecting group.

12. A compound of the formula (I) according to claim 1, wherein m is an integer ranging from 3 to 7.

13. A compound of the formula (I) according to claim 1, wherein the sum of n+m ranges from 5 to 12.

14. A compound of the formula (I) according to claim 1, wherein p is an integer ranging from 0 to 4.

15. A process for the preparation of a compound of formula (I), according to claim 1 or a salt thereof, which comprises:
reacting a compound of formula (XIII):

(XIII)

Wherein Ar is as defined above with a compound of formula (VI):

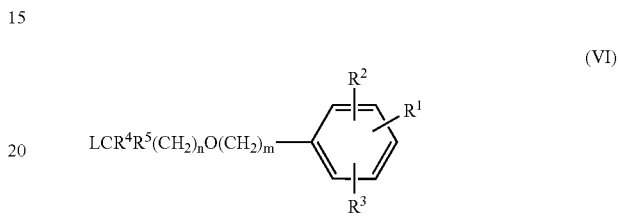

(VI)

wherein L is a leaving group and $R^1$, $R^2$, $R^3$, $R^4$, $R^5$, n and m are as defined for compounds of formula (I);
wherein said process may further optionally comprise one or more of following steps in any order:
(i) removing any protecting groups;
(ii) separating an enantiomer from a mixture of enantiomers;
(iii) converting the product to a corresponding salt, or
(iv) converting a group $R^1$, $R^2$ and/or $R^3$ to another group $R^1$, $R^2$ and/or $R^3$.

16. A process according to claim 15, wherein the leaving group comprises a halo group.

17. A process according to claim 16, wherein the halo group is selected from the group consisting of chloro, bromo, and iodo.

18. A process according to claim 15, wherein the leaving group comprises a sulphonate group.

19. A process according to claim 18, wherein the sulphonate group is a methanesulphonate group.

20. A process for the preparation of a compound of formula (I), according to claim 1, or a salt thereof, which comprises:
reacting a compound of formula (XV):

(XV)

wherein L is a leaving group, with an amine of formula (XVI):

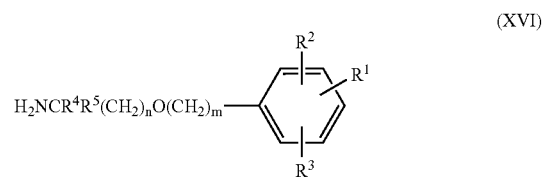

(XVI)

wherein $R^1$, $R^2$ $R^3$, $R^4$, $R^5$, n and m are as defined for formula (I); and wherein said process may further optionally comprise one or more of the following steps in any order:

(i) removing any protecting groups;
(ii) separating an enantiomer from a mixture of enantiomers;
(iii) converting the product to a corresponding salt, or
(iv) converting a group $R^1$, $R^2$ and/or $R^3$ to another group $R^1$, $R^2$ and/or $R^3$.

21. A process according to claim 20, wherein the leaving group comprises a halo group.

22. A process according to claim 20, wherein the halo group is selected from the group consisting of chloro, bromo, and iodo.

23. A process according to claim 20, wherein the leaving group comprises a sulphonate group.

24. A process according to claim 20, wherein the sulphonate group is a methanesulphonate group.

25. A process for the preparation of a compound of formula (I), according to claim 1 or a salt thereof, wherein said process is selected from the group consisting of (i) and (ii):
(i) reacting a compound of formula (XIII):

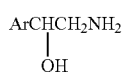

(XIII)

Wherein Ar is as hereinbefore defined and $R^{34}$ is a chiral auxiliary group,
with a compound of formula (XVII):

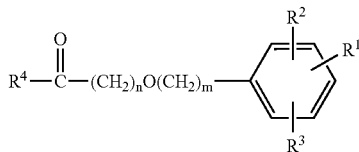

(XVII)

wherein $R^1$, $R^2$ $R^3$, $R^4$, n and m are as hereinbefore defined;
optionally followed by removing said chiral auxiliary group $R^{34}$;
and (ii) reacting a compound of formula (XVIII):

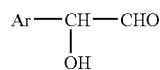

(XVIII)

wherein Ar is as hereinbefore defined; with an amine of formula (XVI):

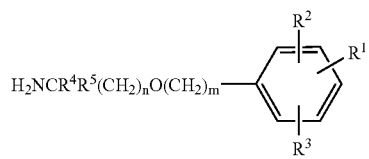

(XVI)

under conditions suitable to effect reductive amination,
wherein said process may further optionally comprise one or more of the following steps in any order:
(i) removing any protecting groups;
(ii) separating an enantiomer from a mixture of enantiomers;
(iii) converting the product to a corresponding salt,
(iv) converting a group $R^1$, $R^2$ and/or $R^3$ to another group $R^1$, $R^2$ and/or $R^3$.

* * * * *